United States Patent
Starkebaum et al.

(10) Patent No.: US 8,538,532 B2
(45) Date of Patent: Sep. 17, 2013

(54) ELECTRICAL STIMULATION THERAPY TO PROMOTE GASTRIC DISTENTION FOR OBESITY MANAGEMENT

(75) Inventors: Warren L. Starkebaum, Plymouth, MN (US); Jiande Chen, Houston, TX (US); Elizabeth D. Firestone, Saint Paul, MN (US); Roland C. Maude-Griffin, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 719 days.

(21) Appl. No.: 12/715,993

(22) Filed: Mar. 2, 2010

(65) Prior Publication Data

US 2010/0228313 A1  Sep. 9, 2010

Related U.S. Application Data

(60) Provisional application No. 61/157,068, filed on Mar. 3, 2009, provisional application No. 61/244,431, filed on Sep. 21, 2009.

(51) Int. Cl.
*A61N 1/36* (2006.01)

(52) U.S. Cl.
USPC .............................. 607/40; 607/116; 607/133

(58) Field of Classification Search
USPC ........................................... 607/40, 116, 133
See application file for complete search history.

(56) References Cited

U.S. PATENT DOCUMENTS

| | | |
|---|---|---|
| 2,865,376 A | 12/1958 | Pellier et al. |
| 3,760,812 A | 9/1973 | Timm et al. |
| 4,444,207 A | 4/1984 | Robicsek |
| 4,475,560 A | 10/1984 | Tarjan et al. |
| 4,524,771 A | 6/1985 | McGregor et al. |
| 4,901,722 A | 2/1990 | Noguchi |
| 5,059,207 A | 10/1991 | Shah |
| 5,100,431 A | 3/1992 | Buster et al. |
| 5,188,104 A | 2/1993 | Wernicke et al. |
| 5,217,471 A | 6/1993 | Burkhart |
| 5,242,458 A | 9/1993 | Bendel et al. |
| 5,263,480 A | 11/1993 | Wernicke et al. |

(Continued)

FOREIGN PATENT DOCUMENTS

| | | |
|---|---|---|
| DE | 44 02 058 | 4/1995 |
| WO | WO 97/41921 | 11/1997 |

(Continued)

OTHER PUBLICATIONS

Yong Lei et al., "Effects and Mechanisms of Implantable Gastric Stimulation on Gastric Distention in Conscious Dogs," Obesity Surgery, vol. 15, pp. 528-533, 2005.

(Continued)

*Primary Examiner* — Carl H Layno
*Assistant Examiner* — Jennifer Ghand
(74) *Attorney, Agent, or Firm* — Shumaker & Sieffert, P.A.

(57) ABSTRACT

In some examples, electrical stimulation therapy is delivered to support obesity management. The electrical stimulation therapy is configured to cause at least partial gastric distention. Gastric distention tends to induce a sensation of fullness and thereby discourages excessive food intake by the patient. The electrical stimulation therapy may be delivered to the gastrointestinal tract of the patient by electrodes deployed by one or more implantable leads coupled to an electrical stimulator. The electrical stimulator delivers stimulation pulses having a pulse width in a range found to be effective in causing gastric distention.

10 Claims, 20 Drawing Sheets

(56) References Cited

U.S. PATENT DOCUMENTS

| | | |
|---|---|---|
| 5,292,344 A | 3/1994 | Douglas |
| 5,423,872 A | 6/1995 | Cigaina |
| 5,423,876 A | 6/1995 | Camps et al. |
| 5,433,728 A | 7/1995 | Kim |
| 5,450,739 A | 9/1995 | Bogart et al. |
| 5,484,404 A | 1/1996 | Schulman et al. |
| 5,489,294 A | 2/1996 | McVenes et al. |
| 5,540,730 A | 7/1996 | Terry, Jr. et al. |
| 5,690,691 A | 11/1997 | Chen et al. |
| 5,716,392 A | 2/1998 | Bourgeois et al. |
| 5,836,994 A | 11/1998 | Bourgeois |
| 5,861,014 A | 1/1999 | Familoni |
| 5,995,872 A | 11/1999 | Bourgeois |
| 6,026,326 A | 2/2000 | Bardy |
| 6,041,258 A | 3/2000 | Cigaina et al. |
| 6,083,249 A | 7/2000 | Familoni |
| 6,091,992 A | 7/2000 | Bourgeois et al. |
| 6,097,984 A | 8/2000 | Douglas |
| 6,098,672 A | 8/2000 | Kiholm |
| 6,104,955 A | 8/2000 | Bourgeois |
| 6,115,635 A | 9/2000 | Bourgeois |
| 6,146,391 A | 11/2000 | Cigaina |
| 6,216,039 B1 | 4/2001 | Bourgeois |
| 6,238,423 B1 | 5/2001 | Bardy |
| 6,243,607 B1 | 6/2001 | Mintchev et al. |
| 6,321,124 B1 | 11/2001 | Cigaina |
| 6,327,503 B1 | 12/2001 | Familoni |
| 6,449,511 B1 | 9/2002 | Mintchev et al. |
| 6,453,199 B1 | 9/2002 | Kobozev |
| 6,510,332 B1 | 1/2003 | Greenstein |
| 6,542,776 B1 | 4/2003 | Gordon et al. |
| 6,564,101 B1 | 5/2003 | Zikria |
| 6,571,127 B1 | 5/2003 | Ben-Haim et al. |
| 6,591,137 B1 | 7/2003 | Fischell et al. |
| 6,600,953 B2 | 7/2003 | Flesler et al. |
| 6,606,523 B1 | 8/2003 | Jenkins |
| 6,615,084 B1 | 9/2003 | Cigaina |
| 6,678,561 B2 | 1/2004 | Forsell |
| 6,684,104 B2 | 1/2004 | Gordon et al. |
| 6,895,278 B1 | 5/2005 | Gordon |
| 6,993,391 B2 | 1/2006 | Flesler et al. |
| 7,006,871 B1 | 2/2006 | Darvish et al. |
| 7,120,497 B2 | 10/2006 | Ben-Haim et al. |
| 7,177,693 B2 | 2/2007 | Starkebaum |
| 7,221,978 B2 | 5/2007 | Ben-Haim et al. |
| 7,330,753 B2 | 2/2008 | Policker et al. |
| 7,502,649 B2 | 3/2009 | Ben-Haim et al. |
| 7,512,442 B2 | 3/2009 | Flesler et al. |
| 7,765,008 B2 | 7/2010 | Ben-Haim et al. |
| 2002/0072780 A1 | 6/2002 | Foley |
| 2002/0161414 A1 | 10/2002 | Flesler et al. |
| 2002/0198470 A1 | 12/2002 | Imran et al. |
| 2003/0009202 A1 | 1/2003 | Levine |
| 2003/0018367 A1 | 1/2003 | DiLorenzo |
| 2003/0054463 A1 | 3/2003 | Baker et al. |
| 2004/0088022 A1 | 5/2004 | Chen |
| 2004/0088023 A1 | 5/2004 | Imran et al. |
| 2004/0162595 A1 | 8/2004 | Foley |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2005/0021101 A1 | 1/2005 | Chen et al. |
| 2005/0033375 A1 | 2/2005 | Marchal et al. |
| 2005/0131486 A1 | 6/2005 | Boveja et al. |
| 2005/0137643 A1 | 6/2005 | Mintchev |
| 2005/0149141 A1* | 7/2005 | Starkebaum .................. 607/40 |
| 2005/0209653 A1 | 9/2005 | Herbert et al. |
| 2005/0222637 A1 | 10/2005 | Chen |
| 2005/0222638 A1 | 10/2005 | Foley et al. |
| 2005/0240239 A1 | 10/2005 | Boveja et al. |
| 2005/0245957 A1 | 11/2005 | Starkebaum et al. |
| 2006/0058856 A1 | 3/2006 | Morrell |
| 2006/0085045 A1 | 4/2006 | Harel et al. |
| 2006/0167498 A1 | 7/2006 | DiLorenzo |
| 2006/0184207 A1 | 8/2006 | Darvish et al. |
| 2006/0247717 A1* | 11/2006 | Starkebaum .................. 607/40 |
| 2006/0247718 A1* | 11/2006 | Starkebaum .................. 607/40 |
| 2006/0257444 A1 | 11/2006 | Tropsha et al. |
| 2006/0257445 A1 | 11/2006 | Tropsha et al. |
| 2006/0257446 A1 | 11/2006 | Tropsha et al. |
| 2007/0027493 A1 | 2/2007 | Ben-Haim et al. |
| 2007/0060812 A1 | 3/2007 | Harel et al. |
| 2007/0078494 A1* | 4/2007 | Mintchev .................. 607/40 |
| 2007/0104754 A1 | 5/2007 | Sterling et al. |
| 2007/0104755 A1 | 5/2007 | Sterling et al. |
| 2007/0150021 A1 | 6/2007 | Chen et al. |
| 2007/0162084 A1 | 7/2007 | Chen et al. |
| 2007/0282387 A1 | 12/2007 | Starkebaum |
| 2007/0299320 A1 | 12/2007 | Policker et al. |
| 2008/0058871 A1 | 3/2008 | Libbus et al. |
| 2008/0178684 A1 | 7/2008 | Spehr |
| 2009/0076561 A1 | 3/2009 | Libbus et al. |
| 2009/0088817 A1 | 4/2009 | Starkebaum et al. |
| 2009/0118797 A1 | 5/2009 | Kliger et al. |
| 2009/0204063 A1 | 8/2009 | Policker et al. |
| 2009/0281449 A1 | 11/2009 | Thrower et al. |
| 2010/0228105 A1 | 9/2010 | Policker et al. |

FOREIGN PATENT DOCUMENTS

| | | |
|---|---|---|
| WO | WO 02/26317 A1 | 4/2002 |
| WO | 02087657 | 11/2002 |
| WO | 2008121891 A1 | 10/2008 |
| WO | WO2009/045294 A1 | 4/2009 |
| WO | WO2009/097542 A2 | 8/2009 |

OTHER PUBLICATIONS

Thirteenth International Workshop on Electrogastrography, Meeting-At-A-Glance, The Feinberg Pavilion, Northwestern University Medical Center, Chicago, Illinois, May 18-19, 2005, 58 pages.

Personalized Itinerary Planner and Abstract Book, DDW, May 20-25, 2006, 127 pages.

Hui Ouyang et al., "Gastric or intestinal electrical stimulation-induced increase in gastric volume is correlated with reduced food intake," Scandinavian Journal of Gastroenterology, vol. 41, pp. 1261-1266, 2006.

Luo et al., "Effects and Mechanisms of Gastric Electrical Stimulation on Gastric Tone in Rats", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).

Chen et al., "Gastric Electrical Stimulation for Obesity: is there a need for a new generation device?", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).

"DDW 2006 Rules for Abstract Submission", Digestive Disease Week 2006, Los Angeles Convention Center, May 20-25, 2006, 3 pages.

Chen et al., "Electrical Pacing Accelerates Intestinal Transit Slowed by Fat-Induced Ileal Brake", Digestive Diseases and Sciences, vol. 48, No. 2, Feb. 2003, pp. 251-256.

Valerio Cigaina, MD., "Implantable Gastric Stimulation for the Treatment of Morbid Obesity", Transneuronix, Inc., Revision 1, Oct. 3, 1999, 12 pages.

Valerio Cigaina, MD., "Implantable Gastric Stimulation for the Treatment of Morbid Obesity", Transneuronix, Inc., Revision 2, Nov. 1, 1999, 11pages.

Chen et al. "Electrical Pacing Accelerates Intestinal Transit Slowed by Fat-Induced Ileal Brake," Digestive Diseases and Sciences, vol. 48, No. 2 (Feb. 2003), pp. 251-256.

Sun et al. "Intestinal Electric Stimulation Decreases Fat Absorption in Rats: Therapeutic Potential for Obesity," Obesity Research, vol. 12, No. 8 (Aug. 2004), pp. 1235-1242.

Lin et al., "Electrical Stimulation of the Small Intestine in Dogs", Proceedings—19th International Conference—IEEE/EMBS, Oct. 30-Nov. 2, 1997, Chicago, IL., 4 pages.

Lei et al., "The effect of short-pulse gastric electrical stimulation (Enterra Therapy) on gastric tone varies with the sites and parameters of stimulation", Transneuronix Inc and Veterans Research Foundation, Oklahoma City, OK, May 2005, 1 page.

Ouyang et al., "Gastrointestinal Electrical Stimulation-Induced Increase in Gastric Volume is Correlated with Reduced Food Intake", Transneuronix and Veterans Research & Education Foundation, Oklahoma City, OK, Mar. 2, 2006, 23 pages.

Notification of Transmittal of the International Search Report and the Written Opinion of the International Searching Authority for corresponding patent application No. PCT/US2010/025863, mailed May 18, 2010, 8 pages.

Lei Yong et al., "Gastric electrical stimulation induced gastric distention in obese rats," BIOSIS/BIOSIS, XP-002579955, Apr. 28, 2010, 2 pages.

Zhang Jing et al., "Central neuronal mechanisms of GES and effects of stimulation parameters and locations in regular and diet-induced obese rats," BIOSIS/BIOSIS, XP-002579956, Apr. 28, 2010, 2 pages.

Office Action for U.S. Appl. No. 11/804,312, mailed Mar. 9, 2011, 9 pages.

Response to office action for U.S. Appl. No. 11/804,312, filed Jun. 9, 2011, 12 pages.

H. Abrahamsson, "Vagal Relaxation of the Stomach Induced from the Gastric Antrum", Acta physiol. scand. 1973, 89, pp. 406-414.

Dickens et al., "Identification of rhythmically active cells in guinea-pig stomach," Journal of Physiology, vol. 514, No. 2, pp. 515-531 (Jan. 1999).

Huizinga, "Gastrointestinal Peristalsis: Joint Action of Enteric Nerves, Smooth Muscle, and Interstitial Cells of Cajal," Microscopy Research and Technique, vol. 47, No. 4, pp. 239-247 (Dec. 1999).

Vantrappen et al., "Gastrointestinal Motility Disorders," Digestive Diseases and Sciences, vol. 31, No. 9, pp. 5S-25S, (Sep. 1986 Supplement).

Shepherd et al., "Electrical stimulation of the auditory nerve: II. Effect of stimulus waveshape on single fibre response properties," Hearing Research 130 (1999): 171-188.

Macherey et al., "Asymmetric Pulses in Cochlear Implants: Effects of Pulse Shape, Polarity, and Rate," JARO 7: 255-266 (2006), pp. 253-266.

Rubinstein et al., "Analysis of Monophasic Biphasic Electrical Stimulation of Nerve," IEEE Transactions on Biomedical Engineering, vol. 48, No. 10, Oct. 2001, pp. 1065-1070.

Shepherd et al., "Chronic Electrical Stimulation of the Auditory Nerve using Non-charge-balanced Stimuli," Acta Otolayngol (Stockh) 1999;119:674-684.

Van Wieringen, "Effects of waveform shape on human sensitivity to electrical stimulation of the inner ear," Hearing Research 200 (2005), pp. 73-86.

McIntyre et al., "Extracellular Stimulation of Central Neurons: Influence of Stimulus Waveform and Frequency on Neuronal Output," J Neurophysiol 88: 1592-1604, 2002.

Eddington et al., "Speech Processors for Auditory Prostheses," NIH Contract NO1-DC-2-1001, Final Progress Report, Jan. 1, 2002-Jun. 30, 2005, 14 pp.

Carlyon et al., "Effect of inter-phase gap on the sensitivity of cochlear implant users to electrical stimulation," Hearing Research 205 (2005), 210-224.

Miller et al., "Electrically evoked single-fiber action potentials from cat: responses to monopolar, monophasic stimulation," Hearing Research 130 (1999), 197-218.

Stylopoulos et al., "Roux-en-Y gastric bypass enhances energy expenditure and extends lifespan in diet-induced obese rats," Obesity, 2009 17(10):1839-47.

Kanno et al., "Rat gastric banding model for bariatric surgery," J Nippon Med Sch. 2008 75(4):202-6.

Endo et al., "An obese rat model of bariatric surgery with gastric banding," Obes Surg. 2007 17(6):815-9.

Monteiro et al., "A rat model of restrictive bariatric surgery with gastric banding," Obes Surg 2006 16(1):48-51.

Monteiro et al., "Rats submitted to gastric banding are leaner and show distinctive feeding patterns," Obes Surg. 2006 16(5):597-602.

Monteiro et al., "Increase in ghrelin levels after weight loss in obese Zucker rats is prevented by gastric banding," Obes Surg. 2007 17(12):1599-607.

Kampe et al., "A rodent model of adjustable gastric band surgery-implications for the understanding of underlying mechanisms," Obes Surg 2009 19(5):625-31.

Lei et al., "Effects of dual pulse gastric electrical stimulation on gastric tone and compliance in dogs," Digestive and Liver Disease, 2008, Dig Liver Dis (2008), doi:10.1016/j.dld.2008.07.312.

Liu et al., "Therapeutic potentials of a novel mthod of dual-pulse gastric electrdical stimulation for gastric dysrhythmia and symptoms of nausea and vomiting," The American Journal of Surgery 191 (2006): 255-261.

Qi et al., "Dual pulse intestinal electrical stimulation normalizes intestinal dysrhythmia and improves symptoms induced by vasopressin in fed state in dogs," Neurogastroenterol Motil (2007) 19: 411-418.

Song et al., "A novel method of 2-channel dual-pulse gastric electrical stimulation improves solid gastric emptying in dogs," Surgery 2008;143:72-8.

Chen, "Gastric Electrical Stimulation With Short Pulses Reduces Vomiting but not Dysrhythmias in Dogs," Gastroenterology 2003;124:401-409.

Chen et al., "Gastric electrical stimulation reduces visceral sensitivity in healthy canines," abstract presented at International Electrogastrography Society, 2005, 1 pg.

Lei et al., "Effects of dual pulses gastric electrical stimulation on gastric tone and compliance," abstract presented at International Electrogastrography Society, 2005, 1 pg.

Qi et al., "Normalization of intestinal dysrhythmia and improvement of symptoms with a novel method of dual pulse intestinal electrical stimulation in dogs," abstract presented at International Electrogastrography Society, 2005, 1 pg.

Song et al., "Effects of dual pulse gastric electrical stimulation on vasopressin-induced dysmotility in dogs," abstract presented at International Electrogastrography Society, 2005, 1 pg.

Final office action for U.S. Appl. No. 11/804,312, mailed Jul. 29, 2011, 7 pages.

Pre-Appeal Brief Request for Review for U.S. Appl. No. 11/804,312, filed Oct. 31, 2011, 3 pages.

Office Action from U.S. Appl. No. 11/804,312, dated Dec. 19, 2011, 6 pp.

Response to Office Action dated Dec. 19, 2011, from U.S. Appl. No. 11/804,312, filed Feb. 21, 2012, 5 pp.

Notice of Allowance from U.S. Appl. No. 11/804,312, dated Mar. 13, 2012, 8 pp.

* cited by examiner

*Note:* Food intake under 4ms-40Hz GES is not significantly different from food intake under 400ms-0.25Hz alone (p=0.22), but all remaining pairwise differences in food intake across treatments are statistically significant (p<0.0001).

ELECTRICAL STIMULATION THERAPY TO PROMOTE GASTRIC DISTENTION FOR OBESITY MANAGEMENT

This application claims the benefit of U.S. Provisional Application No. 61/157,068, entitled, "ELECTRICAL STIMULATION THERAPY TO PROMOTE GASTRIC DISTENTION FOR OBESITY MANAGEMENT," and filed on Mar. 3, 2009, and U.S. Provisional Application No. 61/244,431, entitled, "WAVEFORMS FOR ELECTRICAL STIMULATION THERAPY," and filed on Sep. 21, 2009, the entire contents of each being incorporated herein by reference.

TECHNICAL FIELD

The invention relates to implantable medical devices and, more particularly, implantable medical devices for obesity management.

BACKGROUND

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Certain diseases or conditions can contribute to additional weight gain in the form of fat, or adipose tissue. However, healthy people may also become overweight as a net result of excess energy consumption and insufficient energy expenditure. Reversal of obesity is possible but difficult. Once the patient expends more energy than is consumed, the body will begin to use the energy stored in the adipose tissue. This process will slowly remove the excess fat from the patient and lead to better health. Some patients require intervention to help them overcome their obesity. In these severe cases, nutritional supplements, prescription drugs, or intense diet and exercise programs may not be effective.

Surgical intervention is a last resort treatment for some obese patients who are considered morbidly obese. One common surgical technique is the Roux-en-Y gastric bypass surgery. In this technique, the surgeon staples or sutures off a large section of the stomach to leave a small pouch that holds food. Next, the surgeon severs the small intestine at approximately mid length and attaches the distal section of the small intestine to the pouch portion of the stomach. This procedure limits the amount of food the patient can ingest to a few ounces, and limits the amount of time that ingested food may be absorbed through the shorter length of the small intestine. While this surgical technique may be very effective, it poses significant risks of unwanted side effects, malnutrition, and death.

Electrical stimulation therapy is an alternative to surgical intervention, and may be effective in treating obesity either alone or in combination with diet and exercise. For electrical stimulation therapy, a patient is fitted with an implanted electrical stimulator that delivers electrical stimulation pulses to the patient's stomach via electrodes carried by one or more leads. The electrical stimulation therapy may be configured to induce a sensation of fullness or nausea in the patient, thereby discouraging excessive food intake. In addition, in some cases, the electrical stimulation therapy may be configured to decrease gastric motility so that caloric absorption is reduced. Hence, electrical stimulation therapy may be effective in causing weight loss, by discouraging food intake and/or reducing caloric absorption.

SUMMARY

In general, the invention is directed to techniques for delivering electrical stimulation therapy to support obesity management. The electrical stimulation therapy is configured to cause at least partial gastric distention. Gastric distention tends to induce a sensation of fullness, i.e., satiety, and thereby discourages excessive food intake by the patient. The electrical stimulation therapy may be delivered to the gastrointestinal tract of the patient by electrodes deployed by one or more implantable leads coupled to an external or implantable electrical stimulator.

The electrical stimulator delivers stimulation pulses having a pulse width found to be effective in causing gastric distention. In addition, the pulse width may be selected to promote battery longevity in the implantable electrical stimulator. The pulse width also may be selected to avoid or reduce undesirable side effects. Hence, in some examples, the pulse width may be selected to balance effectiveness in causing gastric distention, power conservation, and avoidance or reduction of undesirable side effects.

In one example, the disclosure is directed to a method comprising generating a plurality of pulse bursts, each of the pulse bursts having a duration of greater than approximately 100 milliseconds, wherein each of the pulse bursts includes a plurality of pulses, each of the pulses having a pulse width of approximately 2 milliseconds to approximately 20 milliseconds, and applying the plurality of pulse bursts to a gastrointestinal tract of a patient to cause gastric distention.

In another example, the disclosure is directed to an implantable gastric stimulator comprising an electrical stimulation pulse generator configured to generate a plurality of pulse bursts, each of the pulse bursts having a duration of greater than approximately 100 milliseconds, wherein each of the pulse bursts includes a plurality of pulses, each of the pulses having a pulse width of approximately 2 milliseconds to approximately 20 milliseconds, and one or more electrodes, coupled to the pulse generator, configured to apply the plurality of pulse bursts to a gastrointestinal tract of a patient to cause gastric distention.

In another example, the disclosure is directed to a computer-readable storage medium comprising instructions that, upon execution, cause a processor to control an electrical stimulation pulse generator to generate a plurality of pulse bursts, each of the pulse bursts having a duration of greater than approximately 100 milliseconds, wherein each of the pulse bursts includes a plurality of pulses, each of the pulses having a pulse width of approximately 2 milliseconds to approximately 20 milliseconds, and apply, via one or more electrodes, the plurality of pulse bursts to a gastrointestinal tract of a patient to cause gastric distention.

In another example, the disclosure is directed to a device comprising means for generating a plurality of pulse bursts, each of the pulse bursts having a duration of greater than approximately 100 milliseconds, wherein each of the pulse bursts includes a plurality of pulses, each of the pulses having a pulse width of approximately 2 milliseconds to approximately 20 milliseconds, and means for applying the plurality of pulse bursts to a gastrointestinal tract of a patient to cause gastric distention.

In an additional example, the disclosure provides a method comprising generating a long electrical stimulation pulse approximated by a plurality of short electrical stimulation pulses, and applying the long electrical stimulation pulse to a gastrointestinal tract of a patient to cause gastric distention.

In another example, the disclosure provides an implantable gastric stimulator comprising an electrical stimulation pulse generator that generates a long electrical stimulation pulse approximated by a plurality of short electrical stimulation pulses, and one or more electrodes, coupled to the pulse generator, that apply the long electrical stimulation pulse to a gastrointestinal tract of a patient to cause gastric distention.

In an additional example, the disclosure provides a method comprising generating an electrical stimulation pulse that both modulates gastric smooth muscle activity and acts through vagal afferent pathways, and applying the electrical stimulation pulse to a gastrointestinal tract of a patient.

In another example, the disclosure provides an implantable gastric stimulator comprising an electrical stimulation pulse generator that generates an electrical stimulation pulse that both modulates gastric smooth muscle activity and acts through vagal afferent pathways, and one or more electrodes, coupled to the pulse generator.

In various examples, the disclosure may provide one or more advantages. For example, delivery of electrical stimulation therapy with a pulse width in a range of greater than or equal to approximately 1 millisecond, more preferably greater than or equal to approximately 1.5 milliseconds and, still more preferably greater than or equal to approximately 2 milliseconds may be effective in promoting gastric distention, e.g., to discourage excessive food intake by a patient and promote weight loss. A pulse width in a range of approximately 1 milliseconds to approximately 50 milliseconds, more preferably in a range of approximately 1.5 milliseconds to approximately 10 milliseconds, more preferably approximately 2 milliseconds to approximately 10 milliseconds, and even more preferably approximately 2 to 5 milliseconds, may be effective in causing gastric distention while promoting better power conservation. Electrical stimulation therapy with pulse widths in the above ranges may be more effective in conserving battery resources, relative to larger pulse widths, increasing longevity of an implanted electrical stimulation device. In addition, relative to larger pulse widths, electrical stimulation therapy having pulse widths in the ranges described above may be more effective in avoiding or reducing adverse side effects in the patient, which can detract from overall therapy and quality of life.

The details of one or more examples of the invention are set forth in the accompanying drawings and the description below. Other features, objects, and advantages of the invention will be apparent from the description and drawings, and from the claims.

DETAILED DESCRIPTION

In general, the invention is directed to techniques for delivering electrical stimulation therapy to support obesity management. The techniques may be embodied, for example, in an electrical stimulation method, an electrical stimulation device, or an electrical stimulation system. The electrical stimulation therapy is configured to cause at least partial gastric distention. In particular, the electrical stimulation therapy is delivered with stimulation pulses having a pulse width in a range found to be effective in causing gastric distention. In addition, the pulse width range may be selected to promote battery longevity in the implantable electrical stimulator. The pulse width also may be selected to avoid or reduce undesirable side effects in the patient. Hence, in some examples, the pulse width may be selected to balance effectiveness in causing gastric distention, power conservation, and avoidance or reduction of undesirable side effects.

As an example, the stimulation pulses may have a pulse width greater than or equal to approximately 2 milliseconds. In other examples, an electrical stimulator delivers stimulation pulses with a pulse width in a range of approximately 2 milliseconds to approximately 20 milliseconds. In further examples, the pulse width is in a range of approximately 2 milliseconds to approximately 10 milliseconds, more preferably approximately 2 milliseconds to 5 milliseconds.

Electrical stimulation having stimulation pulses with pulse widths in the above ranges may be effective in causing gastric distention and thereby discouraging excessive food intake and promoting weight loss while promoting better power conservation. In addition, electrical stimulation therapy with pulse widths in the above ranges may be more effective in conserving battery resources, relative to larger pulse widths, thereby increasing operational longevity of an implanted electrical stimulation device. In addition, relative to larger pulse widths, electrical stimulation therapy having pulse widths in the ranges described above may be more effective in avoiding or reducing adverse side effects in the patient. Examples of side effects caused by larger pulse widths include tremor, nausea, vomiting, pain and abdominal discomfort.

Figure 1:
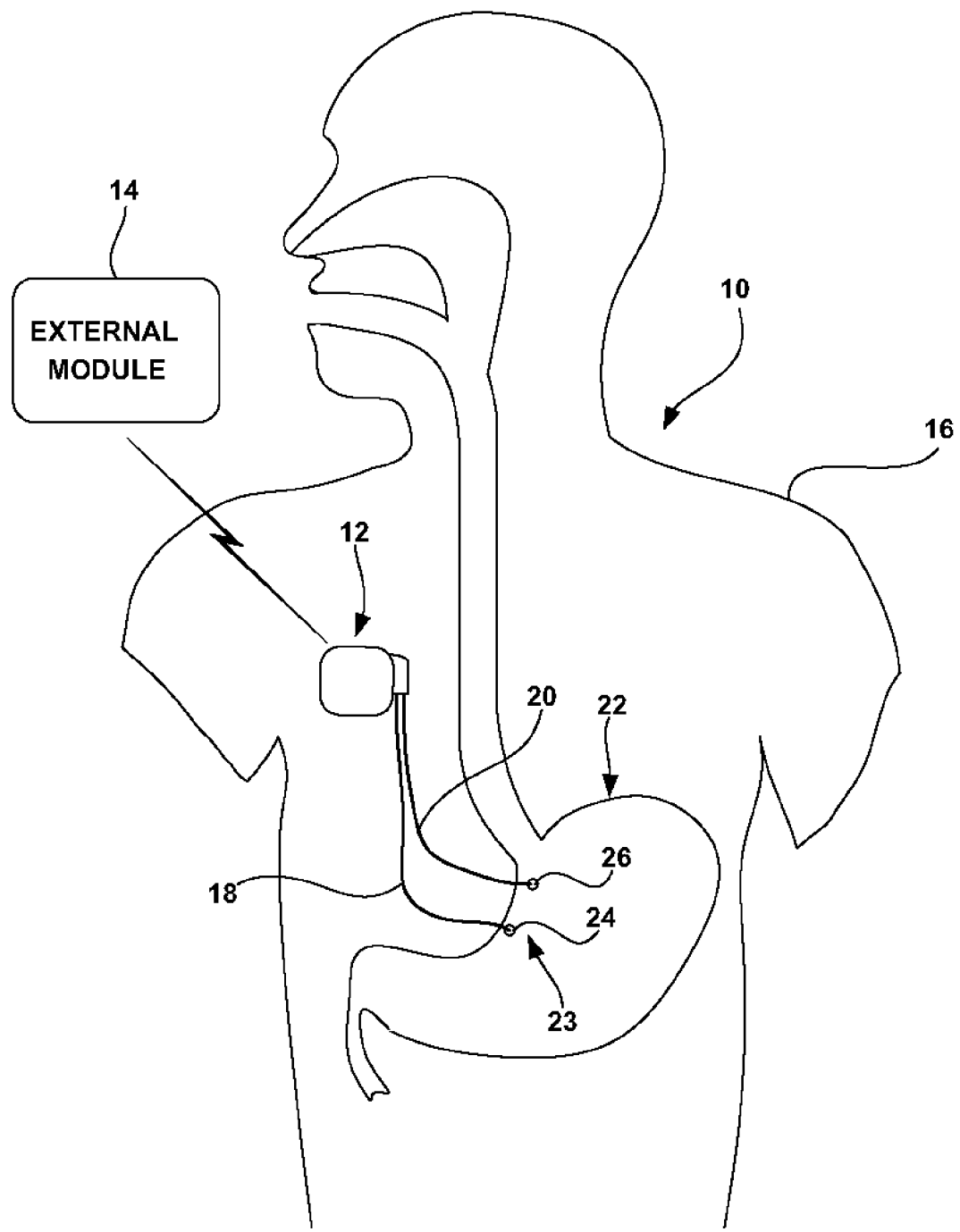
FIG. 1 is a schematic diagram illustrating an implantable gastric stimulation system.

FIG. 1 is a schematic diagram illustrating an implantable stimulation system 10. System 10 is configured to deliver electrical stimulation therapy to support obesity management. The electrical stimulation therapy is configured to cause at least partial gastric distention. Gastric distention generally refers to relaxation and expansion of a portion of the gastrointestinal tract, such as the stomach or small intestine. For purposes of illustration, the disclosure will generally focus on application of electrical stimulation therapy to the stomach, although stimulation may be applied elsewhere in the gastrointestinal tract.

As shown in FIG. 1, system 10 may include an implantable stimulator 12 and an external module 14, both shown in conjunction with a patient 16. Ordinarily, patient 16 is a human patient, as indicated in the example of FIG. 1. Stimulator 12 includes a pulse generator that generates electrical stimulation pulses. In some examples, system 10 may further include a drug delivery device that delivers drugs or other agents to the patient for obesity therapy. One or more implantable leads 18, 20 carry the electrical stimulation pulses from implanted stimulator 12 to stomach 22. In other examples, stimulator 12 may be an external stimulator coupled to percutaneously implanted leads. As a further example, stimulator 12 may be formed as an RF-coupled system in which an external controller provides both control signals and inductively coupled power to an implanted pulse generator.

Leads 18, 20 each include one or more electrodes 24, 26 for delivery of the electrical stimulation pulses to stomach 22. Although the electrical stimulation pulses may be delivered to other areas within the gastrointestinal tract, such as the esophagus, duodenum, small intestine, or large intestine, delivery of stimulation pulses to stomach 22 will generally be described in this disclosure for purposes of illustration. In the example of FIG. 1, electrodes 24, 26 are placed in lesser curvature 23 of stomach 22. For example, electrodes 24, 26 may be placed in lesser curvature 23 approximately 1 centimeter (cm) to approximately 5 cm from the pylorus. Alternatively, or additionally, electrodes 24, 26 could be placed in the greater curvature of stomach 22. For example, electrodes 24, 26 may be placed in the greater curvature approximately 1 centimeter (cm) to approximately 5 cm from the pylorus.

Gastric distention tends to induce a sensation of fullness and thereby discourages excessive food intake by the patient. The therapeutic efficacy of gastric electrical stimulation in managing obesity depends on the stimulation parameters and stimulation target. Electrical stimulation may have mechanical, neuronal and/or hormonal effects that result in a decreased appetite and increased satiety. In turn, decreased appetite results in reduced food intake and weight loss. Gastric distention, in particular, causes a patient to experience a sensation of satiety due to expansion of the stomach, biasing of stretch receptors, and signaling fullness to the central nervous system.

For patient 16 to lose weight, patient 16 must have a net energy such that energy expended is greater than or equal to energy consumed. Diet and exercise play a role in reducing energy consumption. As an alternative or supplement to diet and exercise, stimulator 12 delivers stimulation pulses to the gastrointestinal tract to cause gastric distention. Gastric distention tends to induce a sensation of fullness, and serves to limit food intake by patient 16. Implantable stimulator 12 is configured to deliver stimulation pulses having a pulse width in a range found to be particularly effective in causing gastric distention while promoting battery longevity in the implantable electrical stimulator.

In one example, for example, stimulator 12 delivers stimulation pulses with a pulse width selected to promote gastric distention. As an example, the stimulation pulses delivered by stimulator 12 may have a pulse width greater than or equal to approximately 2 milliseconds. In other examples, an electrical stimulator delivers stimulation pulses with a pulse width in a range of approximately 2 milliseconds to approximately 50 milliseconds. In further examples, the pulse width is in a range of approximately 2 milliseconds to approximately 10 milliseconds, more preferably approximately 2 milliseconds to 5 milliseconds.

The pulse widths in the ranges identified above have been found to be long enough to cause substantial gastric distention. However, the pulse widths are selected to be sufficiently short so that excessive power consumption and adverse patient side effects may be avoided or reduced. In addition, diminishing gains in therapeutic effect may be perceived by patient 16 as the pulse widths become larger. Hence, the pulse width may be selected to balance therapeutic efficacy with reduced power consumption and side effects.

Patient 16 may be successfully treated with stimulation pulses having a range between 1 millisecond and 50 milliseconds. However, patient 16 may receive less efficacious therapy with pulse widths as low as 1 millisecond. In addition, larger pulse widths greater than or equal to 10 milliseconds may cause adverse effects to the patient that may be effective to treat obesity but detract from the patient's quality of life. Example adverse effects may include tremor, nausea, vomiting, gastrointestinal disorders, or other undesirable effects. Moreover, larger pulse widths generally result in a higher rate of power consumption.

For these reasons, patient 16 may be successfully treated with stimulation having pulse widths within a smaller range. For example, patient 16 may be successfully treated with stimulation having a pulse width between approximately 2 milliseconds and 20 milliseconds, between approximately 2 milliseconds and 10 milliseconds, and between approximately 2 milliseconds and 5 milliseconds. Pulse widths of 2 milliseconds and greater may be able to target excitable tissue with strength-duration characteristics not captured with pulse widths smaller than 2 milliseconds in some patients. However, in some cases, patient 16 may perceive adverse side effects with pulse widths substantially greater than or equal to approximately 5 milliseconds. Also, pulse widths greater than or equal to approximately 5 milliseconds may provide diminishing, additional therapeutic benefit over smaller pulse widths less than approximately 5 milliseconds. Accordingly, in these cases, patient 16 may be effectively treated with stimulation pulses having a pulse width between 2 milliseconds and 5 milliseconds, thereby balancing therapeutic efficacy, reduction in adverse side effects, and reduction in power consumption.

Battery longevity in an implantable stimulator is a paramount concern. Implantation of stimulator 12 in patient 16 requires surgery. Similarly, surgery is required for explanation of stimulator 12 in the event battery resources are exhausted, as well as for re-implantation of a replacement stimulator. To reduce the number of surgical operations, and associated pain, recovery time, and risks, it is desirable to preserve battery resources to the extent possible while ensuring therapeutic efficacy. Because shorter pulse widths may reduce power consumption while increasing battery longevity, delivery of stimulation pulses in particular pulse width ranges described in this disclosure may achieve therapeutic efficacy in causing gastric distention while promoting battery longevity.

With further reference to FIG. 1, at the outer surface of stomach 22, e.g., along the lesser curvature 23, leads 18, 20 penetrate into tissue such that electrodes 24 and 26 are positioned to deliver stimulation to the stomach. As mentioned above, the parameters of the stimulation pulses generated by stimulator 12 are selected to distend stomach 22 and thereby induce a sensation of fullness, i.e., satiety. In some examples, the parameters of the stimulation pulses also may be selected to induce a sensation of nausea. In each case, the induced sensation of satiety and/or nausea may reduce a patient's desire to consume large portions of food. Again, the stimulation pulses may be delivered elsewhere within the gastrointestinal tract, either as an alternative to stimulation of lesser curvature 23 of stomach 22, or in conjunction with stimulation of the lesser curvature of the stomach. For example, electrodes 24, 26 may be placed in lesser curvature 23 approximately 1 centimeter (cm) to approximately 5 cm from the pylorus. As one example, stimulation pulses could be delivered to the greater curvature of stomach 22. For example, electrodes 24, 26 may be placed in the greater curvature approximately 1 centimeter (cm) to approximately 5 cm from the pylorus.

The pulse width may be selected so that electrical stimulation, when applied, causes at least a twenty-five percent increase in gastric volume relative to a baseline gastric volume, preferably at least a fifty percent increase in gastric volume, more preferably at least a seventy-five percent increase in gastric volume, and still more preferably at least a one-hundred percent increase in gastric volume. The increase in gastric volume may be measured relative to a baseline gastric volume, such as a preprandial (pre-meal) gastric volume, and may be measured within a selected area of the gastrointestinal tract. For example, the gastric volume may be measured within the stomach if electrical stimulation is applied to the stomach. Alternatively, the baseline and stimulation-induced gastric volume may be measured elsewhere within the gastrointestinal tract.

In addition to pulse width, the stimulation pulses are defined by other parameters including current or voltage amplitude, pulse rate, and duty cycle. In some examples, stimulation parameters may further include electrode combinations and polarities in the event leads 18, 20 provide multiple electrode positions. As an illustration, in addition to a pulse width in the ranges identified above, stimulator 12 may generate stimulation pulses having a current amplitude in a range of approximately less than 1 milliamp (mA) to approximately 20 mA, preferably approximately 1 mA to approximately 15 mA. The pulse rate of the stimulation pulses may be in a range of approximately 2 Hz to 90 Hz, more preferably approximately 2 Hz to 40 Hz, and more preferably approximately 5 Hz to 25 Hz. As described below, a substantial amount of distention may be produced for a pulse width of approximately 2 ms in combination with a pulse rate of approximately 40 Hz.

In addition, stimulator 12 may deliver the stimulation pulses with a duty cycle of approximately 50% ON/50% OFF, preferably 20% ON/80% OFF, and more preferably 100% ON/0% OFF. Duty cycle generally refers to the percentage of time that stimulator 12 is delivering stimulation pulses versus the percentage of time during which the stimulator is idle. During ON time, stimulator 12 delivers pulses according to a set of parameters such as amplitude, pulse rate and pulse width. During OFF time, stimulator 12 does not deliver stimulation pulses to patient 16. In addition, the duty cycle may include multiple levels of delivering stimulation and not delivering stimulation. For example, the duty cycle may include the amount of time pulses are delivered and the amount of time pulses are not delivered to patient 16 when the stimulator 12 is ON. Additionally, a higher level duty cycle includes the amount of time stimulator 12 is ON and OFF. In this manner, example stimulation therapy may have duty cycles that describe when stimulator 12 is ON and OFF in addition to cycles that describe the amount of time pulses are delivered to patient 16 during the ON period.

As one illustration, to cause gastric distention, stimulator 12 may deliver stimulation pulses with a pulse current amplitude of approximately 1 to 15 mA, a pulse width of approximately 2 to 10 milliseconds (ms), a pulse rate of approximately 1 to 60 Hz, and a duty cycle of approximately 25% ON/75% OFF. As another illustration, stimulator 12 may deliver stimulation pulses with an amplitude of approximately 3 to 6 mA, a pulse width of approximately 2 to 5 milliseconds (ms), a pulse rate of approximately 20 to 50 Hz, and a duty cycle of approximately 40% ON/60% OFF. In each case, stimulator 12 will cause substantial gastric distention and a sensation of fullness, resulting in reduced food intake and, ultimately, weight loss.

Implantable stimulator 12 may be constructed with a biocompatible housing, such as titanium, stainless steel, or a polymeric material, and is surgically implanted within patient 16. The implantation site may be a subcutaneous location in the side of the lower abdomen or the side of the lower back. Stimulator 12 is housed within the biocompatible housing, and includes components suitable for generation of electrical stimulation pulses. Stimulator 12 may be responsive to an external module 14 that generates control signals to adjust stimulation parameters. Although stimulator 12 is illustrated as implanted in the example of FIG. 1, in other examples, stimulator 12 may be an external stimulator coupled to percutaneous leads for either trial stimulation or chronic stimulation. As a further example, stimulator 12 may be formed as an RF-coupled system in which an external controller provides both control signals and inductively coupled power to an implanted pulse generator.

Electrical leads 18 and 20 are flexible and include one or more internal conductors that are electrically insulated from body tissues and terminated with respective electrodes 24 and 26 at the distal ends of the respective leads. The leads may be surgically or percutaneously tunneled to stimulation sites on stomach 22. The proximal ends of leads 18 and 20 are electrically coupled to the pulse generator of stimulator 12 via internal conductors to conduct the stimulation pulses to stomach 22 via electrodes 24, 26.

Leads 18, 20 may be placed into the muscle layer or layers of stomach 22 via an open surgical procedure, or by laparoscopic surgery. Leads also may be placed in the mucosa or submucosa by endoscopic techniques or by an open surgical procedure. Electrodes 24, 26 may form a bipolar pair of electrodes. Alternatively, stimulator 12 may carry a reference electrode to form an "active can" arrangement, in which one or both of electrodes 24, 26 are unipolar electrodes referenced to the electrode on the pulse generator. The housing of implantable stimulator 12 may itself serve as a reference electrode. A variety of polarities and electrode arrangements may be used. Each lead 18, 20 may carry a single electrode or an array of electrodes, permitting selection of different electrode combinations and polarities among the leads for delivery of stimulation.

In addition to pulse width, as discussed above, the stimulation pulses delivered by implantable stimulator 12 are characterized by other stimulation parameters such as a voltage or current amplitude and pulse rate. Pulse width and the other stimulation parameters may be fixed, adjusted in response to sensed physiological conditions within or near stomach 22, or adjusted in response to patient or physician input entered via external module 14. For example, in some examples, patient 16 may be permitted to adjust stimulation amplitude, pulse width, or pulse rate and turn stimulation on and off via external module 14.

External module 14 transmits instructions to stimulator 12 via wireless telemetry. Accordingly, stimulator 12 includes telemetry electronics to communicate with external module 14. External module 14 may be a small, battery-powered, portable device that accompanies patient 16 throughout a daily routine. External module 14 may have a simple user interface, such as a button or keypad, and a display or lights. External module 14 may be a hand-held device configured to permit activation of stimulation and adjustment of stimulation parameters.

Alternatively, external module 14 may form part of a larger device including a more complete set of programming features including complete parameter modifications, firmware upgrades, data recovery, or battery recharging in the event stimulator 12 includes a rechargeable battery. External module 14 may be a patient programmer, a physician programmer, or a patient monitor. In some examples, external module 14 may be a general purpose device such as a cellular telephone, a wristwatch, a personal digital assistant (PDA), or a pager.

In some examples, system 10 may include multiple implantable stimulators 12 or multiple leads 18, 20 to stimulate a variety of regions of stomach 22. Stimulation delivered by the multiple stimulators may be coordinated in a synchronized manner, or performed without communication between stimulators. Also, the electrodes may be located in a variety of sites on the stomach, or elsewhere in the gastrointestinal tract, dependent on the particular therapy or the condition of patient 12.

Electrodes 24, 26 carried at the distal ends of lead 18, 20, respectively, may be attached to the wall of stomach 22 in a variety of ways. For example, the electrode may be formed as a gastric electrode that is surgically sutured onto the outer wall of stomach 22 or fixed by penetration of anchoring devices, such as hooks, barbs or helical structures, within the tissue of stomach 22. Also, surgical adhesives may be used to attach the electrodes. In some cases, the electrodes 24, 26 may be placed in the lesser curvature 23 on the serosal surface of stomach 22, within the muscle wall of the stomach, or within the mucosal or submucosal region of the stomach. For example, electrodes 24, 26 may be placed in lesser curvature 23 approximately 1 centimeter (cm) to approximately 5 cm from the pylorus. Alternatively, or additionally, electrodes 24, 26 may be placed in the greater curvature of stomach 22 such that stimulation is delivered to the greater curvature. For example, electrodes 24, 26 may be placed in the greater curvature approximately 1 centimeter (cm) to approximately 5 cm from the pylorus.

In some examples, system 10 may include multiple implantable stimulators 12 to stimulate a variety of regions of stomach 22 or a variety of different regions in the gastrointestinal tract. Stimulation delivered by the multiple stimulators may be coordinated in a synchronized manner, or performed independently without communication between stimulators. As an example, one stimulator may control other stimulators by wireless telemetry, all stimulators may be controlled by external module 14, or the stimulators may act autonomously subject to parameter adjustment or download by external module 14.

Figure 2:
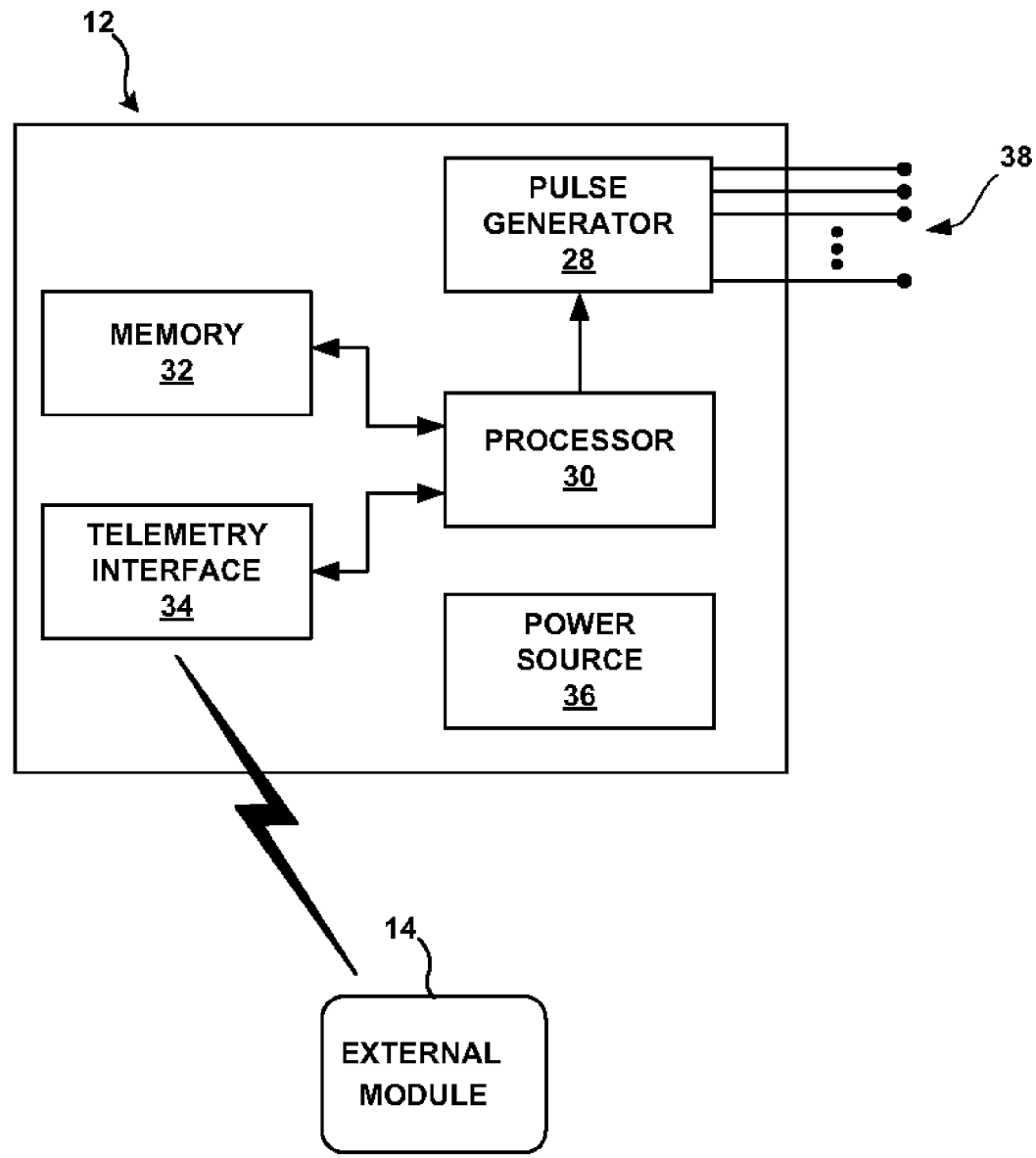
FIG. 2 is a block diagram illustrating exemplary components of an implantable gastric stimulator.

FIG. 2 is a block diagram illustrating implantable stimulator 12 in greater detail in accordance with an example of the invention. In the example of FIG. 2, stimulator 12 includes pulse generator 28, processor 30, memory 32, wireless telemetry interface 34 and power source 36. In some examples, stimulator 12 may generally conform to the Medtronic Itrel 3 Neurostimulator, manufactured and marketed by Medtronic, Inc., of Minneapolis, Minn. However, the structure, design, and functionality of stimulator 12 may be subject to wide variation without departing from the scope of the invention as broadly embodied and described in this disclosure.

Processor 30 controls pulse generator 28 by setting and adjusting stimulation parameters such as pulse amplitude, pulse rate, pulse width and duty cycle. Processor 30 may be responsive to parameter adjustments or parameter sets received from external module 14 via telemetry interface 34. Hence, external module 14 may program stimulator 12 with different sets of operating parameters. In some examples, pulse generator 28 may include a switch matrix. Processor 30 may control the switch matrix to selectively deliver stimulation pulses from pulse generator 28 to different electrodes 38 carried by one or more leads 18, 20. In some examples, stimulator 12 may deliver different stimulation programs to patient 16 on a time-interleaved basis with one another.

Memory 32 stores instructions for execution by processor 30, including operational commands and programmable parameter settings. Memory 32 may include one or more memory modules constructed, e.g., as random access memory (RAM), read-only memory (ROM), non-volatile random access memory (NVRAM), electrically erasable programmable read-only memory (EEPROM), and/or FLASH memory. Processor 30 may access memory 32 to retrieve instructions for control of pulse generator 28 and telemetry interface 34, and may store information in memory 32, such as operational information.

Wireless telemetry in stimulator 12 may be accomplished by radio frequency (RF) communication or proximal inductive interaction of implantable stimulator 12 with external module 14 via telemetry interface 34. Processor 30 controls telemetry interface 34 to exchange information with external module 14. Processor 30 may transmit operational information and receive stimulation parameter adjustments or parameter sets via telemetry interface 34. Also, in some examples, stimulator 12 may communicate with other implanted devices, such as stimulators or sensors, via telemetry interface 34.

Power source 36 delivers operating power to the components of implantable stimulator 12. Power source 36 may include a battery and a power generation circuit to produce the operating power. In some examples, the battery may be rechargeable to allow extended operation. Recharging may be accomplished through proximal inductive interaction between an external charger and an inductive charging coil within implantable stimulator 12. In other examples, an external inductive power supply may transcutaneously power implantable stimulator 12 whenever stimulation therapy is to occur.

Implantable stimulator 12 is coupled to electrodes 38, which may correspond to electrodes 24 and 26 illustrated in FIG. 1, via one or more leads 18, 20. Implantable stimulator 12 provides stimulation therapy to the gastrointestinal tract of patient 16. Pulse generator 28 includes suitable pulse generation circuitry for generating a voltage or current waveform with a selected amplitude, pulse width, pulse rate, and duty cycle. In general, as described in this disclosure, the stimulation pulses generated by pulse generator 28 are formulated with pulse widths suitable to cause substantial gastric distention without excessive consumption of power provided by power source 36.

Figure 3A:
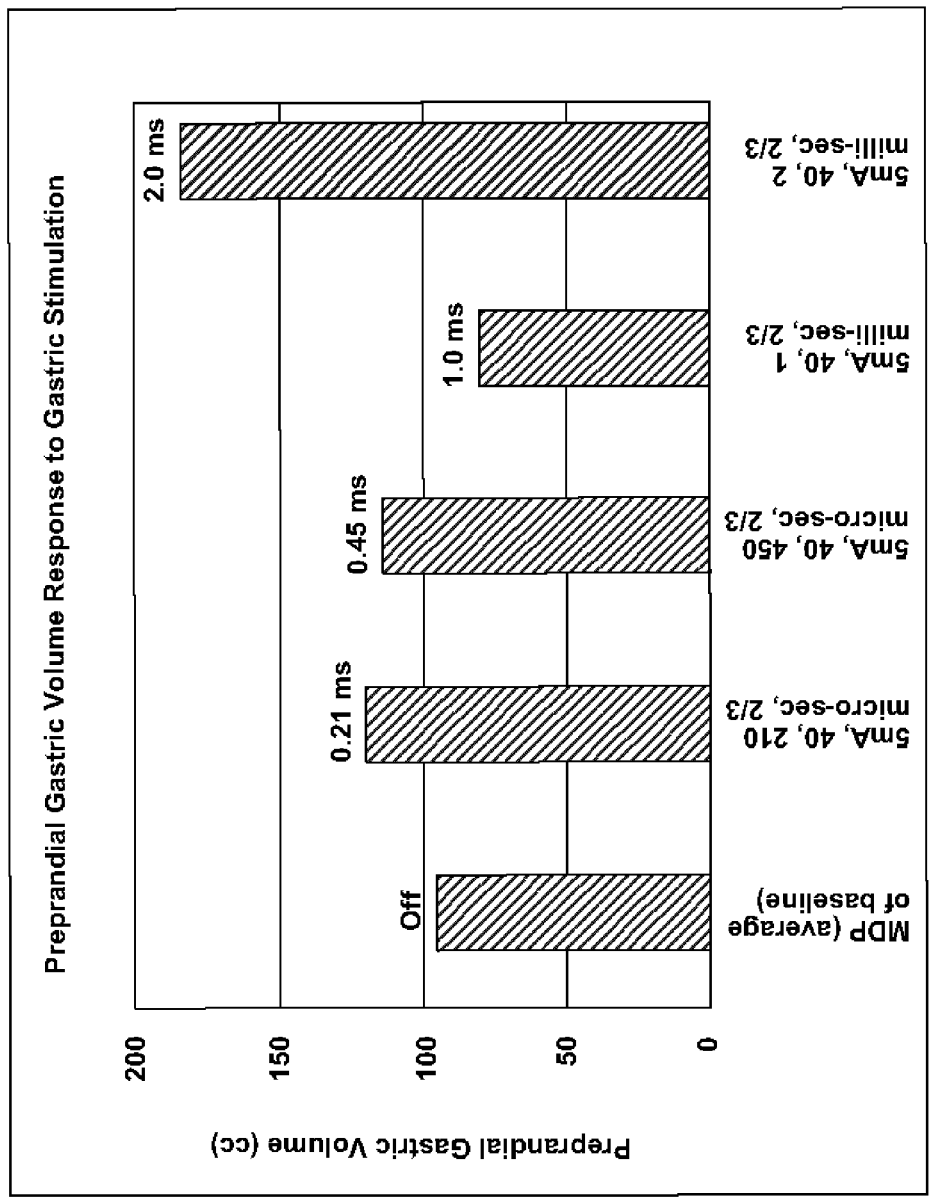
FIG. 3A is a graph illustrating gastric distention response to electrical stimulation therapy with different pulse widths.

FIG. 3A is a graph illustrating gastric distention response to electrical stimulation therapy with different pulse widths. In FIG. 3A, the vertical axis represents the amount of gastric distention caused by different sets of stimulation pulse parameters in terms of preprandial (i.e., pre-meal) gastric volume in cubic centimeters (cc). The horizontal axis shows application of different stimulation parameter sets with substantially constant amplitude, pulse rate and duty cycle values, but varying pulse width values.

The results shown in FIG. 3A are from a canine study. To measure gastric distention, a gastric cannula with an attached balloon was placed in the proximal stomach via a percutaneous gastric port, approximately 10 centimeters (cm) proximal to the pylorus. The balloon was coupled to a barostat to measure gastric distention, e.g., as described in Yong Lei et al., Effects and Mechanisms of Implantable Gastric Stimulation on Gastric Distention in Conscious Dogs, Obesity Surgery, 15, pages 528-533, 2005.

With stimulation OFF, the baseline preprandial gastric volume was approximately 95 cc. In the graph, MDP refers to minimum distending pressure, which is the pressure just above the native abdominal pressure. With stimulation ON, gastric distention induced by electrical stimulation resulted in a gastric volume of approximately 120 cc upon application of stimulation pulses with a pulse amplitude of 5 milliamps (mA), pulse width of 0.21 milliseconds (210 microseconds), pulse rate of 40 Hz, and a duty cycle of 2 seconds ON and 3 seconds OFF (i.e., duty cycle of 40% ON and 60% OFF).

Gastric distention induced by electrical stimulation resulted in an increased gastric volume of approximately 110 cc upon application of stimulation pulses with a pulse amplitude of 5 milliamps (mA), pulse width of 0.45 milliseconds (450 microseconds), pulse rate of 40 Hz, and a duty cycle of 2 seconds ON and 3 seconds OFF (i.e., duty cycle of 40% ON and 60% OFF). Gastric distention induced by electrical stimulation resulted in an increased gastric volume of approximately 80 cc upon application of stimulation pulses with a pulse amplitude of 5 milliamps (mA), pulse width of 1.0 milliseconds, pulse rate of 40 Hz, and a duty cycle of 2 seconds ON and 3 seconds OFF (i.e., duty cycle of 40% ON and 60% OFF).

Notably, for a pulse width of 2 milliseconds, with a pulse amplitude of 5 milliamps (mA), pulse rate of 40 Hz, and a duty cycle of 2 seconds ON and 3 seconds OFF (i.e., duty cycle of 40% ON and 60% OFF), the gastric distention induced by electrical stimulation resulted in an increased gastric volume of approximately 180 cc. The approximate 180 cc volume caused by the 2 ms pulse width resulted in an increase in gastric volume of almost 100% relative to the baseline gastric volume of approximately 95 cc. Accordingly, as shown in FIG. 3A, assuming common amplitudes, pulse rates and duty cycles, different pulse widths appear to have different impacts on the degree of gastric stimulation induced by electrical stimulation. In particular, to achieve more substantial gastric distention, it is desirable to increase the pulse width to a value greater than or equal to 1 millisecond (ms). More particularly, a more substantial degree of gastric distention was observed with a pulse width of 2 ms.

To avoid excessive power consumption, however, it is generally undesirable to apply stimulation pulses with very large pulse widths. Therefore, in accordance with an example of the invention, stimulator 12 may be configured, programmed, or otherwise constructed to deliver stimulation pulses with pulse widths selected to cause substantial gastric distention without consuming excessive amounts of power. As an example, the stimulation pulses delivered by stimulator 12 may have a pulse width greater than or equal to approximately 2 milliseconds. In other examples, an electrical stimulator delivers stimulation pulses with a pulse width in a range of approximately 2 milliseconds to approximately 10 milliseconds. In further examples, the pulse width is in a range of approximately 2 milliseconds to 5 milliseconds.

Although higher pulse widths, e.g., 300 milliseconds, may cause as much or even more distention than pulse widths in the ranges described in this disclosure, the resulting power consumption is excessive, undermining device longevity due to the need for premature battery replacement. In addition, larger pulse widths may be more difficult to produce using existing electrical stimulation devices. Instead, larger pulse widths may require substantial redesign of pulse generator circuitry, which is generally undesirable. Further, larger pulse widths may cause undesirable adverse effects in patient 16 that prevent the overall therapy from being efficacious. Possible adverse effects may include tremors, nausea, vomiting, and/or other gastrointestinal changes. Various examples of the invention may provide a balance between therapeutic efficacy, power consumption, and pulse generator complexity.

Stimulator 12 may be configured to operate in either a voltage control mode or a current control mode. In a current control mode, a substantially constant current amplitude may be maintained for the pulses. For example, a constant current amplitude of approximately 5 mA is described in some of the examples in this disclosure. In a voltage control mode, a substantially constant voltage amplitude may be maintained for the pulses. For example, an appropriate voltage corresponding to approximately 5 mA can be determined by measuring the impedance of the leads and electrodes, and computing the voltage as voltage=current×impedance. Hence, stimulator 12 may deliver constant current or constant voltage stimulation pulses. As further illustration, example stimulation may be delivered over a 500 ohm impedance in patient 16. In this example, one example may include a voltage range between 0.5 Volts (V) and 10V. In another example, the voltage range may be between 1V and 5V. In an additional example, the voltage range may be between 1.5V and 3V. These voltage ranges may be applicable to constant current amplitude examples or constant voltage examples.

Gastric stimulation has been shown to invoke a gastric distention response. Short pulse width (PW) stimulation results in a modest gastric distention response (GDR), while very wide pulse width stimulation results in maximal gastric distention response, but excessive power consumption. It is presumed that the GDR/PW curve has a sigmoid shape, which may allow for determination of the lowest power settings to invoke a desired GDR response.

In some examples, pulses may be delivered in bursts of pulses during the ON portion of the duty cycle. The pulse train may be delivered in a variety of different modes, such as a continuous mode, an asynchronous burst mode, or a synchronous burst mode. In a continuous mode, the pulse train is delivered relatively continuously over an active period in which stimulation is "ON." In an asynchronous burst mode, the pulse train is delivered in periodic bursts during the active period. The continuous mode and asynchronous burst mode may be considered open loop in the sense that they do not rely on synchronization with sensed events.

In a synchronous burst mode, the pulse train is delivered in bursts that are synchronized with a sensed event, such as a sensed physiological condition such as gastric contraction. In this sense, the synchronous burst mode may be viewed as a closed loop approach. For example, leads 18, 20 or different leads may carry one or more sensors, such as sense electrodes, piezoelectric electrodes, strain gauge sensors, accelerometers, pressure sensors, ultrasonic sensors or the like. Such sensors may sense physiological one or more conditions, such as gastric contractions, gastric nerve potentials, or gastric pressure, that indicate the intake of food. In response, stimulator 12 may activate stimulation to cause gastric distention and thereby discourage the intake of excessive amounts of food. Sensing may occur continuously, periodically, or intermittently, as therapy dictates. Information relating to the sensed conditions may be stored in memory within stimulator 12 or external module 14 for retrieval and analysis at a later time.

The active period for delivery of stimulation pulses each mode may be full-time, part-time, or subject to patient control. The active period is different from a duty cycle. The duty cycle applies during an active period, and represents the time that the stimulation is ON versus the time the stimulation is OFF during the active period. During an inactive period, no stimulation is delivered. For part-time activation, the stimulation may be activated for selected parts of the day. The selected parts of the day may coincide with meal times, physical activity times, sleep times, or other selected times, and be controlled using a clock within stimulator 12 or external module 14.

Additionally, or alternatively, patient 16 may control stimulator 12 via external module 16 to activate delivery of stimulation pulses, e.g., when the patient 16 intends to ingest a meal. Also, in some examples, patient 16 may be permitted to adjust one or more stimulation parameters such as amplitude, pulse width, pulse rate, or duty cycle, and turn stimulation on and off. In other cases, if the patient lacks sufficient discipline or capacity to effectively activate and adjust stimulation, stimulator 12 may operate without substantial patient intervention.

Figure 3B:
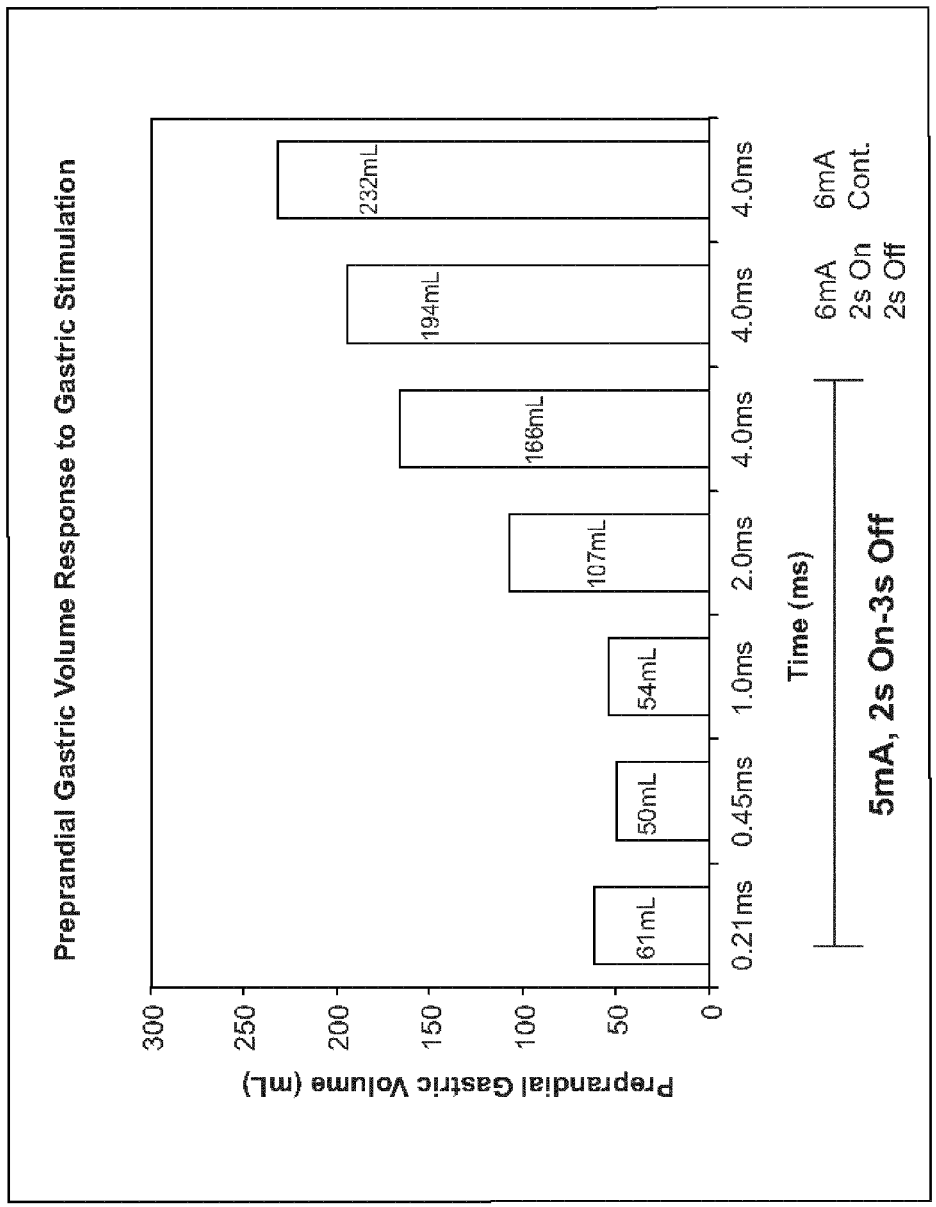
FIG. 3B is another graph illustrating gastric distention response to electrical stimulation therapy with different pulse widths.

FIG. 3B is another graph illustrating gastric distention response to electrical stimulation therapy with different pulse widths, pulse amplitudes, and stimulation duty cycles. In FIG. 3B, the vertical axis represents change in preprandial (i.e., pre-meal) gastric volume caused by different sets of stimulation pulse parameters in terms of gastric volume in milliliters. The horizontal axis represents the width of the stimulation pulse in milliseconds (ms). With stimulation ON, gastric distention induced by electrical stimulation resulted in a gastric volume of approximately 61 milliliters upon application of stimulation pulses with a pulse amplitude of 5 milliamps (mA), pulse width of 0.21 milliseconds (210 microseconds), and a duty cycle of 2 seconds ON and 3 seconds OFF (i.e., duty cycle of 40% ON and 60% OFF). Changing only the pulse width of the stimulation to 0.45 milliseconds resulted in a gastric volume of approximately 50 milliliters. Changing only the pulse width of the stimulation to 1.0 millisecond resulted in a gastric volume of approximately 54 milliliters. Changing only the pulse width of the stimulation to 2.0 milliseconds resulted in a gastric volume of approximately 107 milliliters. Changing only the pulse width of the stimulation to 4.0 milliseconds resulted in a gastric volume of approximately 166 milliliters.

Referring still to FIG. 3B, gastric distention induced by electrical stimulation resulted in a gastric volume of approximately 194 milliliters upon application of stimulation pulses with a pulse amplitude of 6 milliamps (mA), pulse width of 4.0 milliseconds, and a duty cycle of 2 seconds ON and 2 seconds OFF (i.e., duty cycle of 50% ON and 50% OFF). Notably, gastric distention induced by electrical stimulation resulted in a gastric volume of approximately 232 milliliters upon application of stimulation pulses with a pulse amplitude of 6 mA, pulse width of 4.0 milliseconds, and a continuous duty cycle (i.e., 100% ON and 0% OFF).

Figure 4:
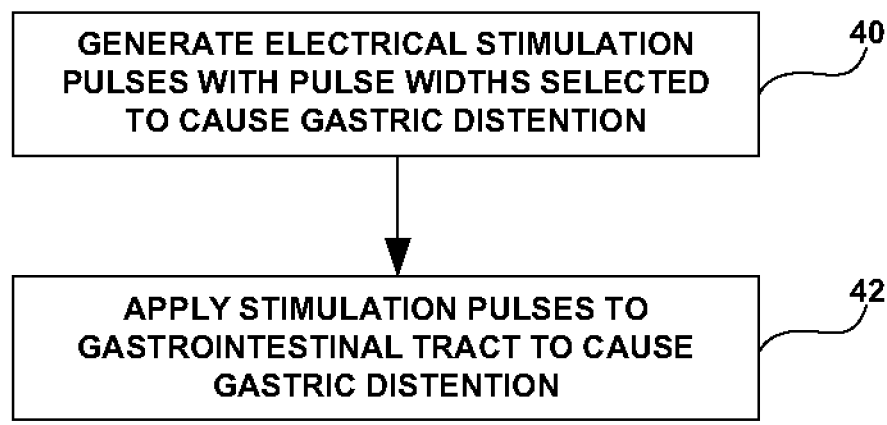
FIG. 4 is a flow diagram illustrating a method for delivering electrical stimulation having a pulse width selected to cause substantial gastric distention.

FIG. 4 is a flow diagram illustrating a method for delivering electrical stimulation having a pulse width selected to cause substantial gastric distention. As shown in FIG. 4, the method may include generating electrical stimulation pulses with pulse widths selected to cause gastric distention (40). As described in this disclosure, the stimulation pulses may have a pulse width greater than or equal to approximately 2 milliseconds. In other examples, an electrical stimulator delivers stimulation pulses with a pulse width in a range of approximately 2 milliseconds to approximately 10 milliseconds, more preferably approximately 2 milliseconds to 5 milliseconds. The method may further include applying the stimulation pulses to the gastrointestinal tract to cause gastric distention (42), e.g., via one or more electrodes carried by one or more implantable leads. The electrical stimulation pulses may be applied to the stomach, or to other areas within the gastrointestinal tract, such as the esophagus, duodenum, small intestine, or large intestine.

Gastric distention may generally refer to as an increase in gastric volume or a relaxation in gastric muscle tone. Hence, a volumetric change associated with gastric distention may be indicative of a state or relaxation of gastric muscle tone. In general, in accordance with this disclosure, gastric distention, increase in gastric volume and relaxation of gastric muscle tone may be used interchangeably to generally refer to a relative state of contraction or relaxation of the stomach muscle.

The state of contraction or relaxation of the stomach muscle may be evaluated using a device called a balloon barostat. The Distender Series II™, manufactured by G&J Electronics, Inc., Toronto, Ontario, Canada, is an example of a balloon barostat system that may be used to diagnose certain gastric motility disorders. Using this system, a balloon is inserted into the stomach, and inflated to a pressure just above the abdominal pressure, referred to the minimum distending pressure. The barostat is configured so that the pressure in the balloon is maintained at a constant pressure. If the state of contraction of stomach muscle decreases, i.e., the state of relaxation of the stomach muscle increases, then the balloon volume will increase. A decrease in the state of stomach muscle contraction, if measured under conditions of constant balloon pressure, indicates a change in gastric muscle tone, i.e., gastric muscle relaxation, and is sometimes referred to as a change in gastric distention, gastric volume, or gastric tone.

More particularly, a decrease in muscle contraction corresponds to an increase in muscle relaxation and promotes distention in terms of an increase in gastric volume using balloon barostat evaluation.

Figure 5A:
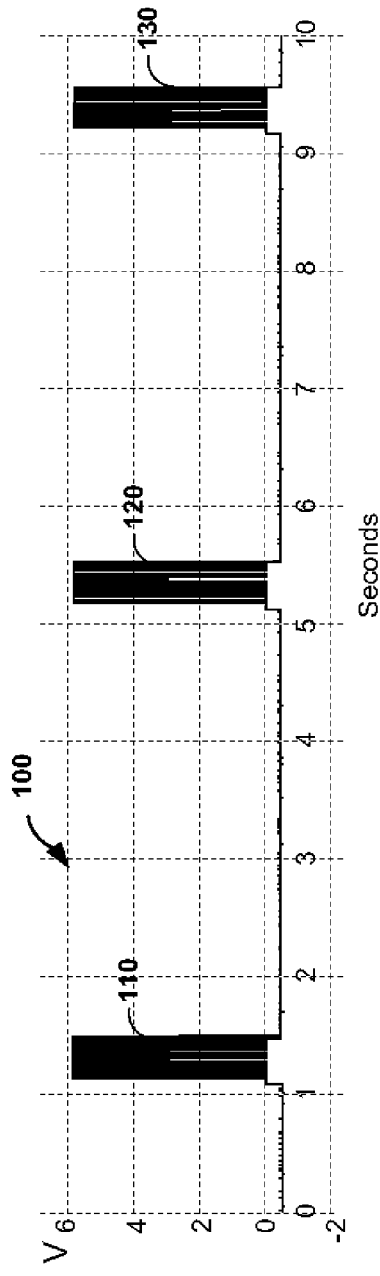
FIG. 5A is a graph illustrating an example of an electrical stimulation pulse train for treating obesity using a short pulse train to approximate a long pulse.

FIG. 5A is a graph illustrating an example waveform for treating obesity in accordance with the disclosure. Rather than use a long pulse to provide electrical stimulation, a short pulse burst may be used to approximate or simulate a long pulse, as in FIG. 5A. A long pulse, low frequency gastric electrical stimulation (GES) paradigm effectively modulates gastric smooth muscle activity, while a short pulse, high frequency GES paradigm may act primarily through vagal afferent pathways. A combination of these GES paradigms, given their distinct effects, has larger effects on gastric tone than either alone.

For reference, a long pulse may be characterized as having a pulse width greater than approximately 100 milliseconds and less than approximately 600 milliseconds, and a short pulse may be characterized as having a pulse width greater than approximately 2 milliseconds and less than approximately 20 milliseconds. Additionally, a low frequency may be characterized as having a pulse rate in a range between approximately 0.1 hertz (Hz) and approximately 1 Hz, and a high frequency may be characterized as having a pulse rate of greater than approximately 2 Hz and less than approximately 200 Hz.

In FIG. 5A, one example of a short pulse burst used to approximate a long pulse is depicted. The y-axis of FIG. 5A represents the pulse voltage amplitude of the waveform comprising a plurality of pulse bursts in volts and the x-axis represents time in seconds. A plurality of pulse bursts 100 is shown including 3 pulse bursts 110, 120, 130, each having a pulse voltage amplitude of approximately 6 volts. In FIG. 5A, pulse bursts 110, 120, 130 are separated by approximately 4 seconds, and begin at approximately 1 second, 5 seconds, and 9 seconds, respectively, from the start of a sequence. Each pulse burst 110, 120, 130 may be used to approximate a 300 millisecond ("long") pulse having a pulse rate of approximately 0.25 Hz.

It should be noted that that the waveform depicted in FIG. 5A is charged balanced. Charge balance may generally refer to the property of the net charge of two or more stimulation pulses being approximately equal to zero. For example, when a pair of single phase pulses having opposite polarity are substantially charged balanced, the charge of the first pulse substantially offsets the charge of the second pulse such that the net charge of the pulses is substantially zero. Graphically, in terms of two pulses having opposite polarity, charge balance implies that the net area under the amplitude vs. time curve is zero. In general, charge balance may be desirable for limiting electrochemical reactions on the surface of the stimulation electrodes that can cause corrosion of the electrodes, formation of noxious compounds at the stimulation site, and transfer of electrode material into the surrounding tissue. As seen in FIG. 5A, pulse trains 110, 120, and 130 are charge balanced because the area defined by each of pulse trains 110, 120, and 130 is equal to the area below 0 volts between each of pulse trains 110, 120, and 130.

Gastric electrical stimulation (GES) may refer to stimulation of the stomach, as well as stimulation of other regions within the gastrointestinal tract (e.g., small intestine).

Figure 5B:
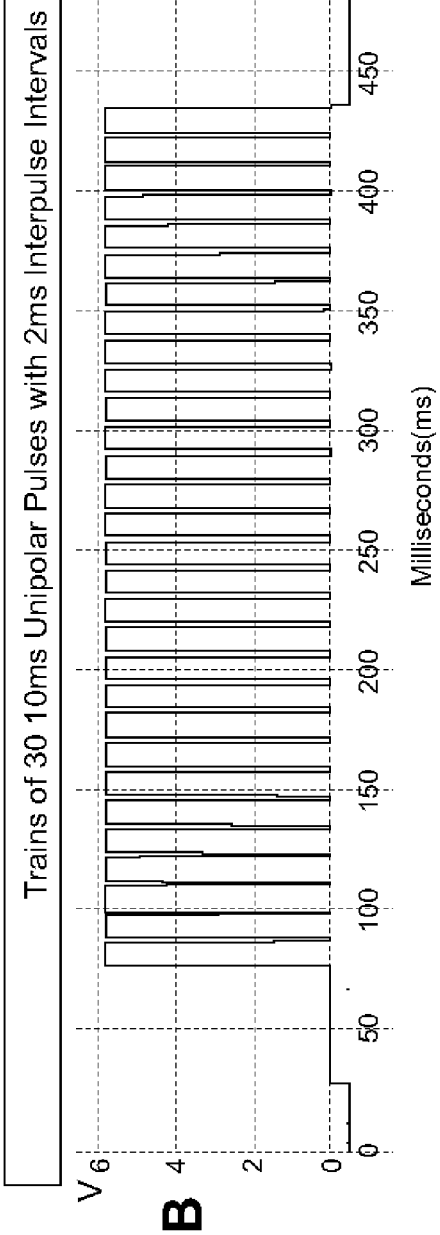
FIG. 5B is a graph illustrating the short pulse train in FIG. 5A in greater detail.

FIG. 5B is a graph depicting a short pulse burst (e.g., 110, 120, 130) of FIG. 5A in greater detail. The y-axis of FIG. 5B represents the pulse voltage amplitude of the pulse burst in volts and the x-axis represents time in milliseconds. In FIG. 5B, thirty pulses (forming, for example one of short pulse bursts 110, 120, 130 of FIG. 5A) having a pulse width of approximately 10 milliseconds, a pulse voltage amplitude of approximately 6 volts, and a 2 millisecond interpulse interval between pulses, are depicted. The pulse burst begins at approximately 75 milliseconds and ends at approximately 430 milliseconds.

Waveform 100 shown in FIG. 5A is just one example of a plurality of pulse bursts that may be used to promote gastric distention in accordance with the disclosure. As will be described in more detail below, parameters of the pulse bursts and waveform may be varied within certain operating ranges to produce desirable effects.

Short pulses bursts used to approximate or simulate a long pulse may have larger effects on gastric tone than either short pulses or long pulses alone. In a canine study, the effect of long pulse, low frequency stimulation was compared to the effect of short pulse burst approximation of long pulse stimulation and very short pulse burst approximation of long pulse stimulation. A very short pulse burst is a subset of a short pulse burst. The combined treatments described below are hybrids of long pulse, low frequency GES and short pulse, high frequency GES in which long pulses (e.g. a stimulation pulse having a pulse width of about 400 milliseconds) are approximated by isoenergetic short pulse bursts.

Platinum-iridium wire electrodes were implanted in the gastric antrum of 10 canine subjects. A gastric cannula was also implanted for balloon barostat measurements of gastric distension. Percutaneous lead wires and an external pulse generator were used to deliver 3 isoenergetic (600 μC/s) variants of GES: a long pulse setting having a pulse width of 400 milliseconds and a pulse rate of 0.25 Hz; a short pulse burst setting having a pulse width of 10 milliseconds, a pulse rate of 83 Hz, and a duty cycle of 0.48 seconds ON and 3.52 seconds OFF that replaced each long pulse of 400 milliseconds with a train of forty 10-millisecond pulse bursts; and, a very short pulse burst setting having a pulse width of 1 millisecond, a pulse rate of 500 Hz, and a duty cycle of 0.8 seconds ON and 3.2 seconds OFF that replaced each long pulse of 400 milliseconds with a train of four-hundred 1-millisecond pulses. The pulse current amplitude was generated by a constant current source and fixed at 6 milliamps (mA) for long pulses, short pulse bursts, and very short pulse bursts. The pulse voltage amplitude was approximately 6 volts.

Figure 6:
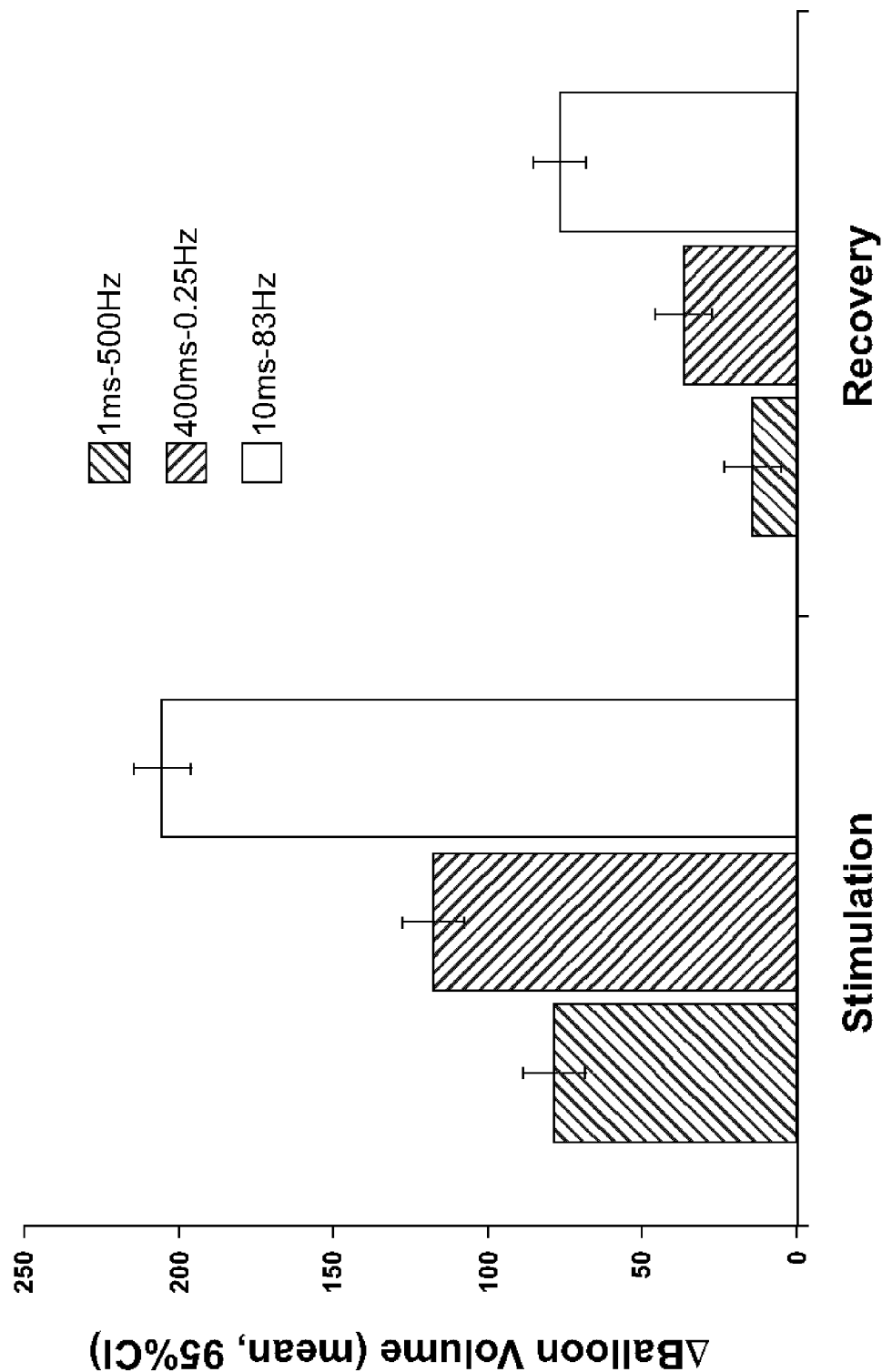
FIG. 6 is a bar graph depicting the mean change in balloon volume for three isoenergetic variants of gastric electrical stimulation (GES) during both stimulation and recovery in lean canines.
Figure 7:
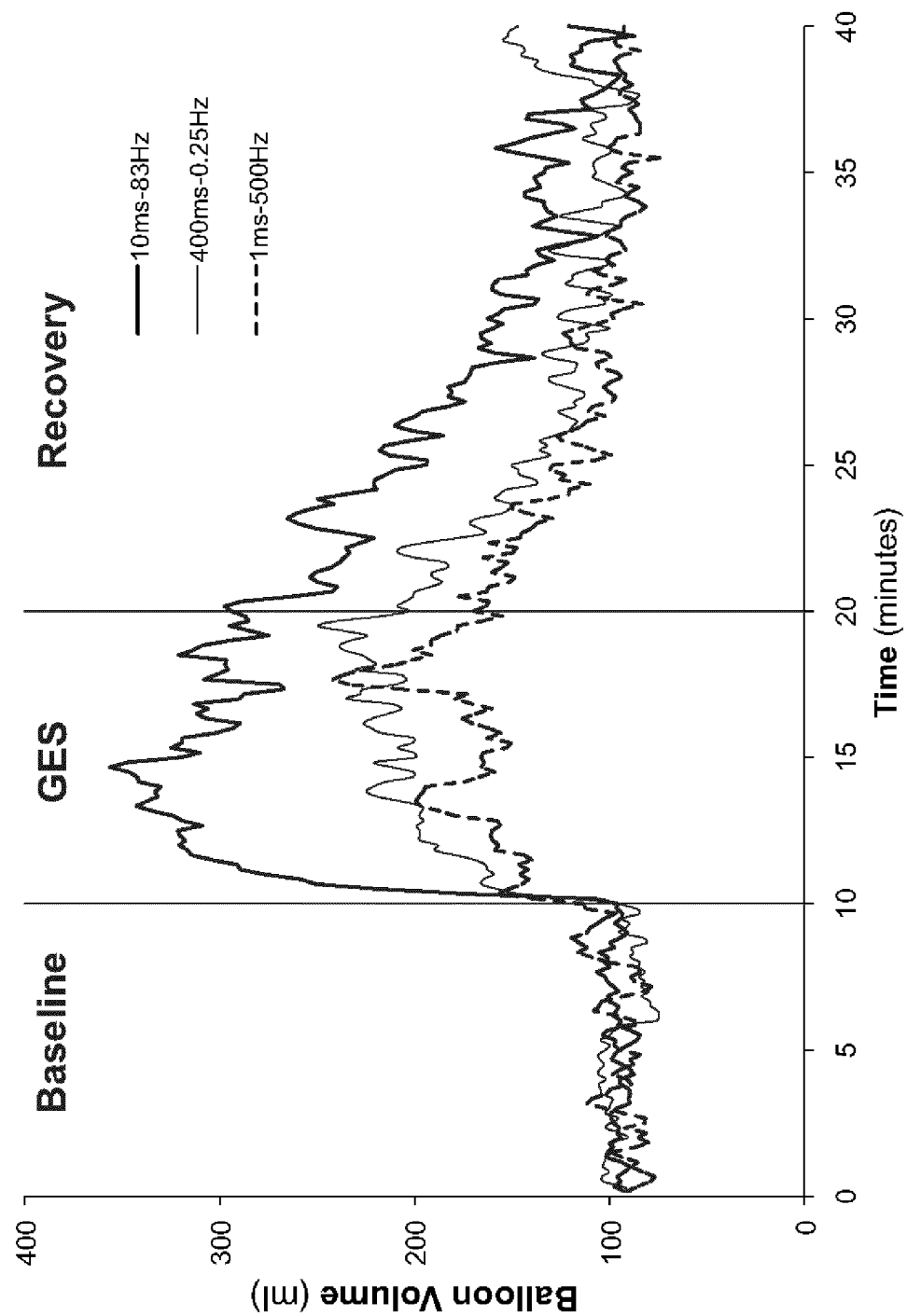
FIG. 7 is a graph comparing the balloon volumes resulting from the application of the three isoenergetic variants of GES, beginning from a pre-GES baseline, and continuing through GES and recovery in lean canines.

Results of the study are shown graphically in FIGS. 6 and 7. In FIG. 6, the mean change in balloon volume, as an indication of amount of distension, is depicted for each of the 3 isoenergetic variants of GES described above, during both stimulation and recovery in lean canines From left to right during the stimulation portion as well as the recovery portion, the change in balloon volume is depicted for the very short pulse burst setting, the long pulse setting, and the short pulse burst setting. As seen in FIG. 6, the change in balloon volume is greater after application of the short pulse burst setting than either the long pulse or very short pulse burst settings.

FIG. 7 graphically compares the balloon volumes resulting from the application of the 3 isoenergetic variants of GES described above, beginning from a pre-GES baseline, and continuing through GES and recovery in lean canines. In FIG. 7, the y axis represents the balloon volume in milliliters and the x-axis represents time in minutes. Relative to pre-GES baseline levels, gastric distention induced by electrical stimulation caused volume increases by approximately 108 ml upon application of stimulation pulses with a pulse width of 400 milliseconds and a pulse rate of 0.25 Hz. Relative to pre-GES baseline levels, gastric distention induced by electrical stimulation increased by approximately 78 ml under application of stimulation pulses that approximated each long pulse of 400 milliseconds with a train of 400 1 millisecond pulses, each of the 400 pulses having a pulse width of 1 millisecond, a pulse rate of 500 Hz, and a duty cycle of 0.8 seconds ON and 3.2 seconds OFF.

Notably, under application of stimulation pulses that approximated each long pulse of 400 milliseconds with forty 10 millisecond pulses, each of the 40 pulses having a pulse width of approximately 10 milliseconds, a pulse rate of 83 Hz, and a duty cycle of 0.48 seconds ON and 3.52 seconds OFF, gastric distention induced by electrical stimulation increased by approximately 285 ml relative to pre-GES baseline levels. The approximate 285 ml volume increase caused by a series of pulse bursts, where each pulse burst consisted of 40 pulses having a pulse width of 10 milliseconds to approximate a 400 ms pulse width, resulted in a gastric distention response more than 2.5 times larger than that achieved by applying stimulation pulses with an actual pulse width of 400 milliseconds and a pulse rate of 0.25 Hz. The train of 400 1 millisecond pulses, with each of the 400 pulses having a pulse width of 1 millisecond, a pulse rate of 500 Hz, and a duty cycle of 0.8 seconds ON and 3.2 seconds OFF, was significantly less effective than either the stimulation pulses with an actual pulse width of 400 milliseconds and a pulse rate of 0.25 Hz or the train of forty 10 millisecond pulses to approximate a 400 millisecond pulse rate, each of the 40 pulses having a pulse width of 10 milliseconds. Thus, a hybrid version of GES that combines elements of long pulse-low frequency and short pulse-high frequency stimulation paradigms may be more effective than long pulse GES in inducing gastric distention. Combining GES modalities that alter acute gastrointestinal (GI) function via differing pathways may be one means for improving the efficacy of GES as a treatment for obesity or gastroparesis.

Of course, the specific example described above with respect to the canine study is only one example of an electrical stimulation waveform using a plurality of short pulse bursts, with each short pulse burst approximating a long pulse, for treating obesity. The stimulation waveform and the pulse bursts are not limited to the specific parameters described above. Rather, implantable stimulator 12 is configured to deliver stimulation pulses using stimulation parameters within certain operating ranges.

In some examples, for example, stimulator 12 may be configured to deliver stimulation pulses with interpulse intervals in a range of approximately 200 microseconds to approximately 2 milliseconds, and more preferably approximately 500 microseconds to approximately 2 milliseconds. In some examples, stimulator 12 delivers stimulation pulses at a frequency such that the interpulse intervals are less than 2 milliseconds. In each case, the interpulse interval generally refers to the time between successive pulses, e.g., the time between the fall of one pulse and the rise of the next pulse.

In some examples, stimulator 12 delivers stimulation pulses with pulse widths within a range of approximately 2 milliseconds to approximately 20 milliseconds. In other examples, the pulse width is in a range of approximately 2 milliseconds to approximately 10 milliseconds. And in further examples, the pulse width is in a range of approximately 2 milliseconds to approximately 5 milliseconds.

In one example, stimulator 12 delivers stimulation pulses with a pulse current amplitude in a range between approximately less than 1 milliamp and approximately 20 milliamps. In other examples, the pulse current amplitude is in a range between approximately 1 milliamps and approximately 15 milliamps. In further examples, the pulse current amplitude is in a range between approximately 5 milliamps and approximately 9 milliamps.

In some examples, stimulator 12 delivers stimulation pulses with a pulse voltage amplitude in a range between approximately 3 volts and approximately 12 volts. In other examples, the pulse voltage amplitude is in a range between approximately 4 volts and approximately 10 volts. In further examples, the pulse voltage amplitude is in a range between approximately 5 volts and approximately 8 volts.

In one example, stimulator 12 delivers stimulation pulses at a pulse rate such that the interpulse interval is in a range of approximately 200 microseconds to approximately 2 milliseconds. The interpulse interval is the time from the trailing edge of one pulse to the leading edge of the next pulse. The frequency is the inverse of the period, which is the sum of the pulse width and the interpulse interval. Because the period is the time from the leading edge of one pulse to the leading edge of the next, it includes the pulse width and the interpulse interval. By way of example, for pulses with a 2 millisecond pulse width and a 2 millisecond interpulse interval, the period is 4 milliseconds and the frequency is 1/(4 milliseconds), or about 250 Hz. In other examples, the frequency range of pulses may be between approximately 2 Hz and approximately 90 Hz. In other examples, the frequency range may be between approximately 2 Hz and approximately 40 Hz. In some examples, the frequency range may be between approximately 5 Hz and approximately 25 Hz.

As mentioned above, a short pulse burst may be used to approximate or emulate a long pulse. Because long pulses typically have pulse widths greater than 100 milliseconds, e.g., between approximately 100 milliseconds and approximately 600 milliseconds, the short pulse burst approximation of the long pulse may also have a duration of between approximately 100 milliseconds and approximately 600 milliseconds. In some examples, stimulator 12 delivers short pulse burst approximations having a duration between approximately 200 milliseconds and approximately 550 milliseconds. In further examples, stimulator 12 delivers short pulse burst approximations having a duration between approximately 300 milliseconds and approximately 500 milliseconds.

In some examples, a short pulse burst may be delivered as an isoenergetic plurality of bursts in order to approximate the energy delivered by a long pulse. As such, any duty cycle may be chosen that results in a short pulse burst delivering approximately the same energy as a long pulse. Thus, the duty cycle of the short pulse width pulse burst may be chosen based on the long pulse that is being approximated. In some examples, each short pulse burst has a pulse rate of approximately 5 Hz to approximately 50 Hz.

Figure 8A:
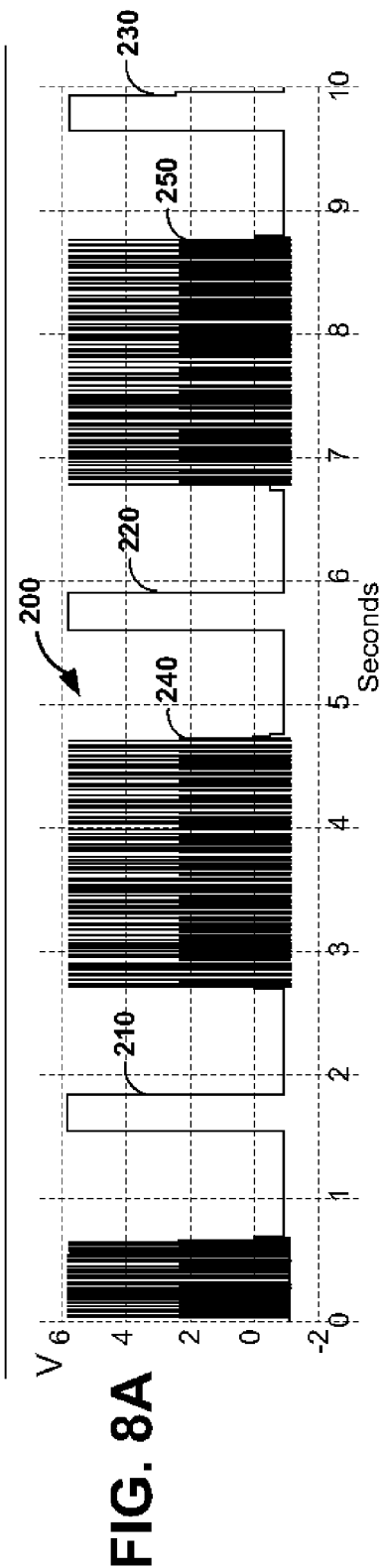
FIG. 8A is a graph illustrating an example of an electrical stimulation pulse train for treating obesity using a pattern of a long pulse followed by a train of short pulses.

FIG. 8A is a graph illustrating another example of an electrical stimulation waveform for treating obesity in accordance with the disclosure. Rather than using long pulses alone to provide electrical stimulation, a pattern of a long pulse followed by a short pulse burst followed by a long pulse followed by a short pulse bursts, etc. may be used, as seen in FIG. 8A. In some examples, the pattern may repeat. In this example, a short pulse burst is delivered between successive long pulses. A long pulse, low frequency GES paradigm effectively modulates gastric smooth muscle activity, while a short pulse, high frequency GES appears to act primarily through vagal afferent pathways. A combination of these GES paradigms, given their distinct effects, may result in greater food intake and acute gastrointestinal (GI) effects than either modality alone.

A long pulse may be characterized as having a pulse width greater than approximately 100 milliseconds and less than approximately 600 milliseconds, and a short pulse may be characterized as having a pulse width greater than approximately 1 millisecond and less than approximately 20 milliseconds. In some examples, stimulator 12 delivers long pulses with each long pulse having a pulse width in the range of approximately 100 milliseconds to approximately 600 milliseconds. In other examples, the pulse width is in a range of approximately 200 milliseconds to approximately 550 milliseconds. In further examples, the pulse width in the range of approximately 300 milliseconds to approximately 500 milliseconds. In some examples, stimulator 12 delivers short stimulation pulses with pulse widths within a range of approximately 2 milliseconds to approximately 20 milliseconds. In other examples, the pulse width is in a range of approximately 2 milliseconds to approximately 10 milliseconds. And in further examples, the pulse width is in a range of approximately 2 milliseconds to approximately 5 milliseconds.

Additionally, a low frequency may be characterized as having a pulse rate in a range between approximately 0.1 Hz and approximately 1 Hz, and a high frequency may be characterized as having a pulse rate of greater than approximately 2 Hz and less than approximately 200 Hz. In other examples, a low frequency pulse rate is in a range of approximately 0.15 Hz to approximately 0.8 Hz. In further examples, a low frequency pulse rate is in a range of approximately 0.2 Hz to approximately 0.4 Hz. In some examples, the high frequency pulse rate is in a range of approximately 25 Hz to approximately 100 Hz. In other examples, the high frequency pulse rate is in a range of approximately 30 Hz to approximately 90 Hz.

In one example, the short pulse burst is delivered between a range of approximately 1 second and approximately 20 seconds. In other examples, the short pulse burst is delivered between a range of approximately 5 seconds and approximately 15 seconds. In some examples, the short pulse bursts is delivered between a range of approximately 10 seconds and approximately 12 seconds.

In FIG. 8A, the y-axis represents the pulse voltage amplitude of the pulse train in volts and the x-axis represents time in seconds. Electrical stimulation waveform 200 includes long pulses 210, 220, 230, each with a pulse width of approximately 300 milliseconds, a pulse voltage amplitude of approximately 6 volts, and long pulses being separated by approximately 4 seconds. Electrical stimulation waveform 200 further includes short pulse bursts 240, 250, each having a pulse voltage amplitude of approximately 6 volts, following long pulses 210, 220, respectively. Short pulse burst 240 begins at approximately 2.6 seconds and short pulse burst 250 begins at approximately 6.6 seconds. Each pulse burst 240, 250 may have a pulse width of approximately 4 milliseconds, a pulse rate of approximately 40 Hz, and a duty cycle of approximately 2 seconds ON and 2 seconds OFF.

Figure 8B:
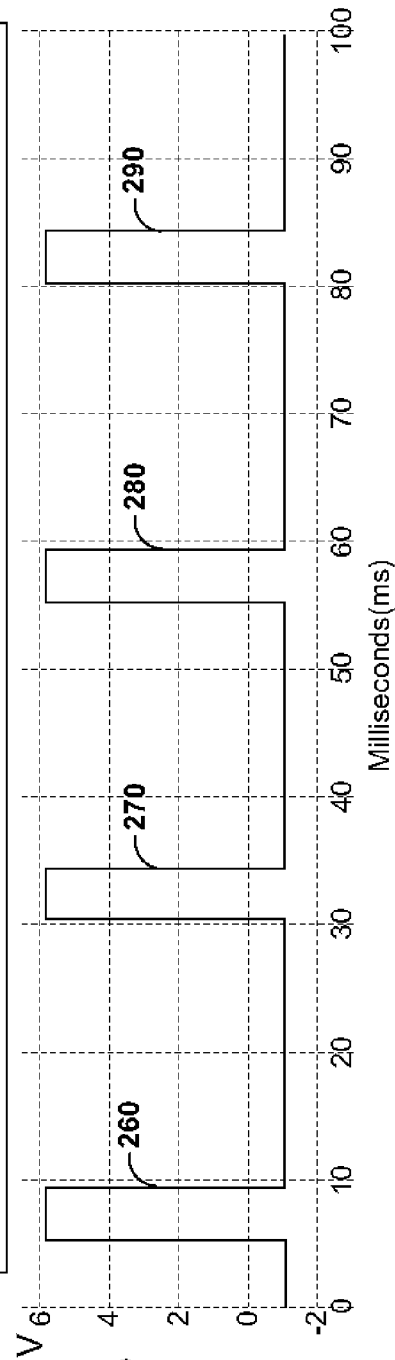
FIG. 8B is a graph illustrating the short pulses of FIG. 6B in greater detail.

FIG. 8B depicts the pulses that form short pulse burst 240, 250 of FIG. 8A in more detail. The y-axis represents the pulse voltage amplitude of the pulse burst in volts and the x-axis represents time in milliseconds. In FIG. 8B, 4 pulses 260, 270, 280, 290 are depicted with each pulse having a pulse width of approximately 4 milliseconds, an interpulse interval of approximately 20 milliseconds, and a pulse voltage amplitude of approximately 6 volts.

Electrical stimulation waveform 200 shown in FIG. 8A is just one example of a waveform including a plurality of pulse bursts between long pulses that may be used to promote gastric distention in accordance with the disclosure. As will be described in more detail below, parameters of the stimulation pulses and pulse bursts may be varied within certain operating ranges to produce desirable effects.

As mentioned above, a combination of long pulse, low frequency GES and short pulse, high frequency GES paradigms may have greater food intake and acute gastrointestinal (GI) effects than either modality alone. In a canine study, the effect of long pulse, low frequency stimulation was compared to the effect of short pulse, high frequency pulse trains alone, and the combination of long pulse, low frequency and short pulse, high frequency pulse trains. Platinum-iridium wire electrodes were implanted in the gastric antrum of 10 canine subjects. A gastric cannula was also implanted for balloon barostat measurements of GD and monitoring of antral motility (AM) via manometric catheter. Percutaneous lead wires and an external pulse generator were used to deliver 3 variants of GES: a long pulse setting having a pulse width of 400 milliseconds and a pulse rate of 0.25 Hz; a short pulse burst setting with each pulse of the pulse burst having a pulse width of 4 milliseconds, a pulse rate of 40 Hz, and a duty cycle of 2 seconds ON and 2 seconds OFF; and a combination setting that combines a long pulse setting and a short pulse burst setting, having a long pulse with pulse width of 400 milliseconds and a pulse rate of 0.25 Hz and a short pulse burst with each pulse of the pulse burst having a pulse width of 4 milliseconds, a pulse rate of 40 Hz, and a duty cycle of 2 seconds ON and 2 seconds OFF, with long pulses centered between short pulse trains. Gastric distention was measured under all 3 settings while AM and food intake were measured under the long pulse and combination settings. Pulse amplitude was fixed at 6 mA in the gastric distention and food intake studies, and at 8 mA during AM testing.

Figure 9:
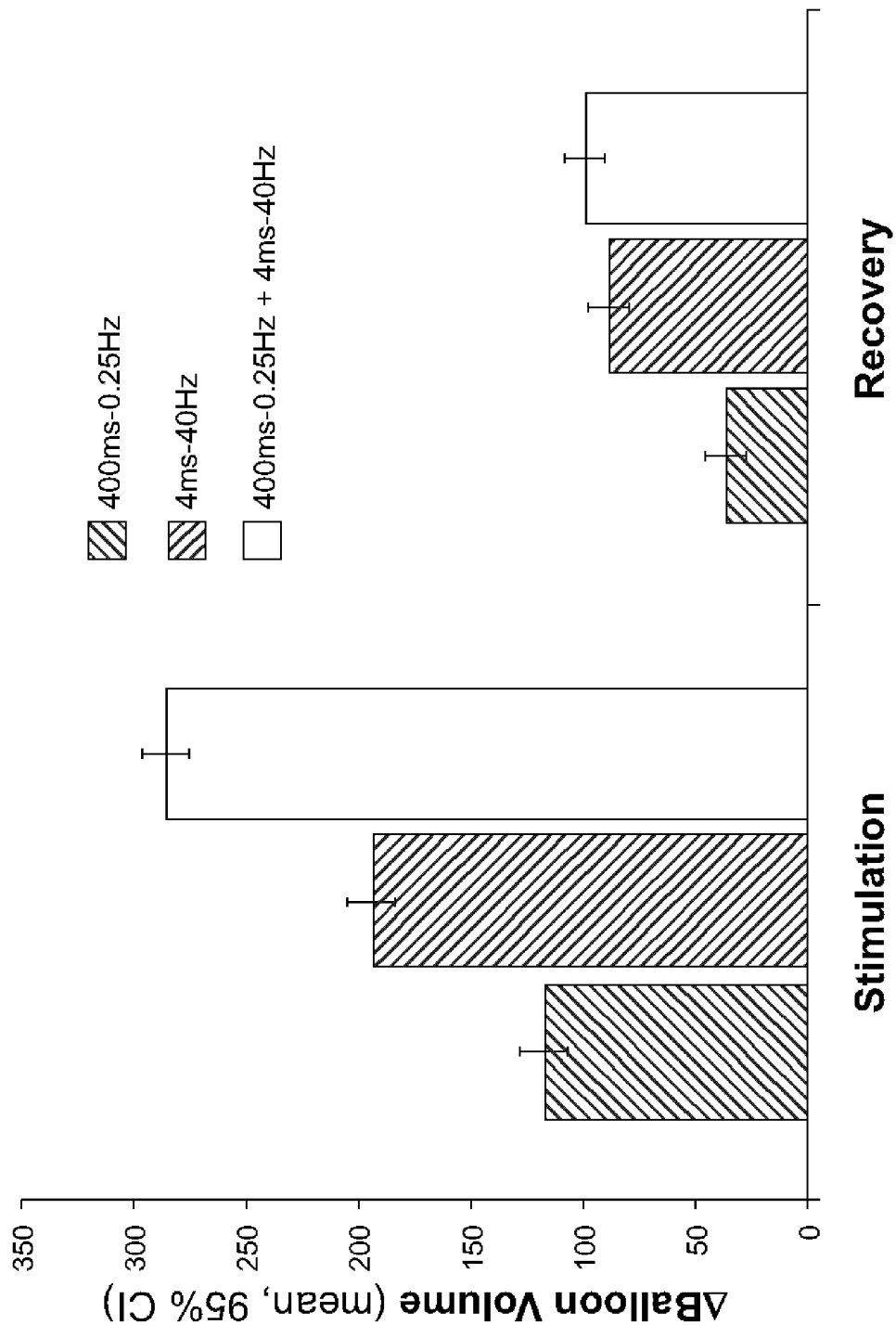
FIG. 9 is a bar graph depicting the mean change in balloon volume for three isoenergetic variants of GES, during both stimulation and recovery after stimulation in lean canines.
Figure 10:
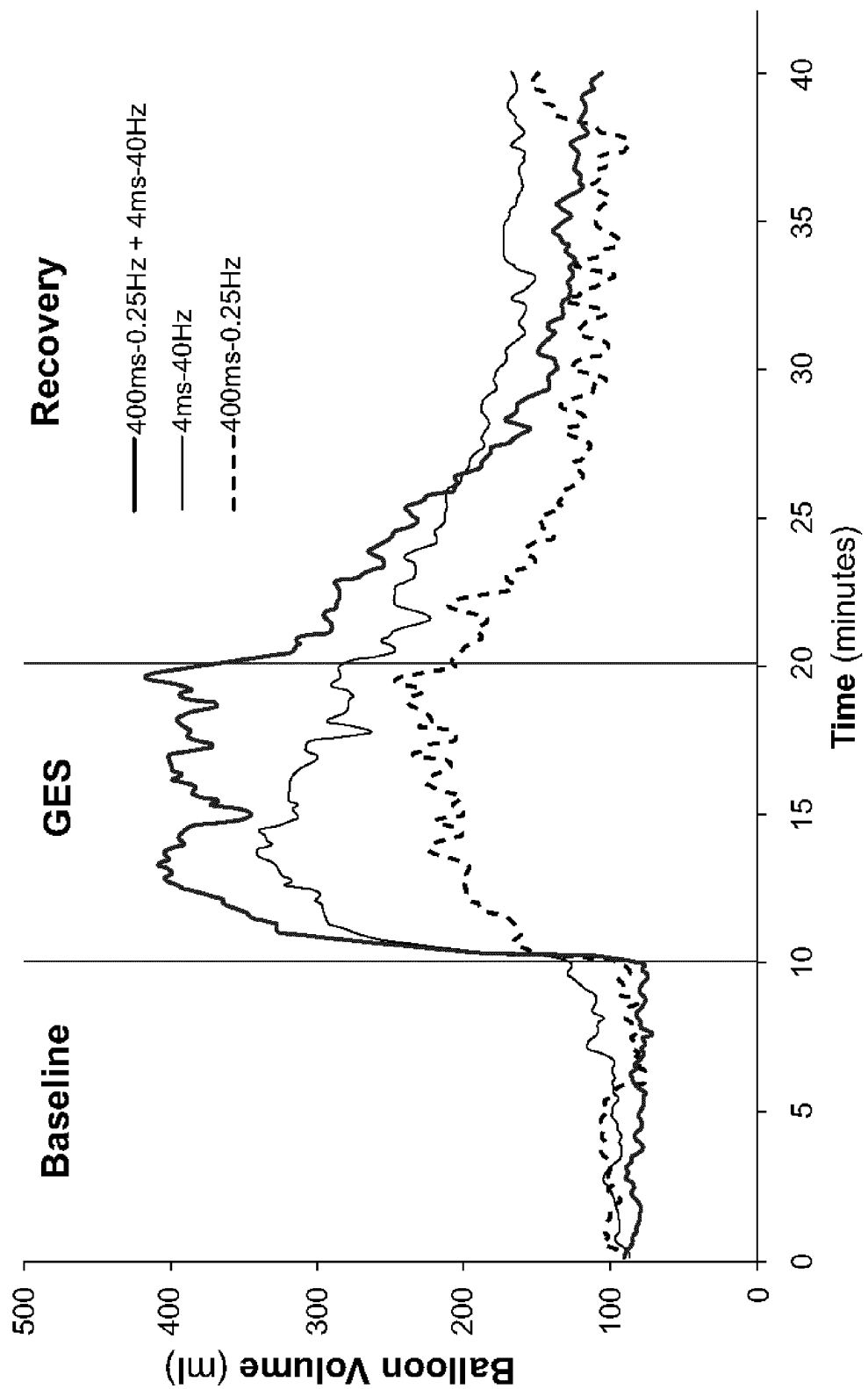
FIG. 10 is a graph comparing the balloon volumes resulting from the application of the three isoenergetic variants of GES, beginning from a pre-GES baseline, and continuing through GES and recovery in lean canines.

Results of the study are shown graphically in FIGS. 9 and 10. In FIG. 9, the mean change in balloon volume is depicted for each of the 3 isoenergetic variants of GES described above, during both stimulation and recovery after stimulation in lean canines. From left to right during the stimulation portion as well as the recovery portion, the change in balloon volume is depicted for the long pulse setting, the short pulse burst setting, and the combination of long and short pulse burst setting. As seen in FIG. 9, the mean change in balloon volume is greater after application of the combination setting than either the long pulse setting or the short pulse burst settings.

FIG. 10 compares the balloon volumes resulting from the application of the 3 isoenergetic variants of GES described above, beginning from a pre-GES baseline, and continuing through GES and recovery in lean canines. In FIG. 10, the y axis represents the balloon volume in milliliters and the x-axis represents time in minutes. Relative to pre-GES baseline levels, gastric distention induced by electrical stimulation increased by approximately 108 ml upon application of stimulation pulses with a pulse width of 400 milliseconds and a pulse rate of 0.25 Hz. Relative to pre-GES baseline levels, gastric distention induced by electrical stimulation increased by approximately 195 ml upon application of stimulation pulses with a pulse width of 4 milliseconds, a pulse rate of 40 Hz, and a duty cycle of 2 seconds ON and 2 seconds OFF.

Notably, under application of the combination setting stimulation pulses having a long pulse with a pulse width of 400 milliseconds and a pulse rate of 0.25 Hz and a short pulse burst with each pulse of the pulse burst having a pulse width of 4 milliseconds, a pulse rate of 40 Hz, and a duty cycle of 2 seconds ON and 2 seconds OFF, with long pulses centered between short pulse bursts, gastric distention induced by electrical stimulation increased by approximately 285 ml relative to pre-GES baseline levels. In some examples, the long pulses are not centered between short pulse bursts. Rather, the long pulses are offset between short pulse bursts. In one example, there may be more time between the trailing edge of a short pulse burst and the leading edge of a long pulse than between the trailing edge of the long pulse and the leading edge of the next short pulse burst. In another example, there may be less time between the trailing edge of a short pulse burst and the leading edge of a long pulse than between the trailing edge of the long pulse and the leading edge of the next short pulse burst.

Figure 11:
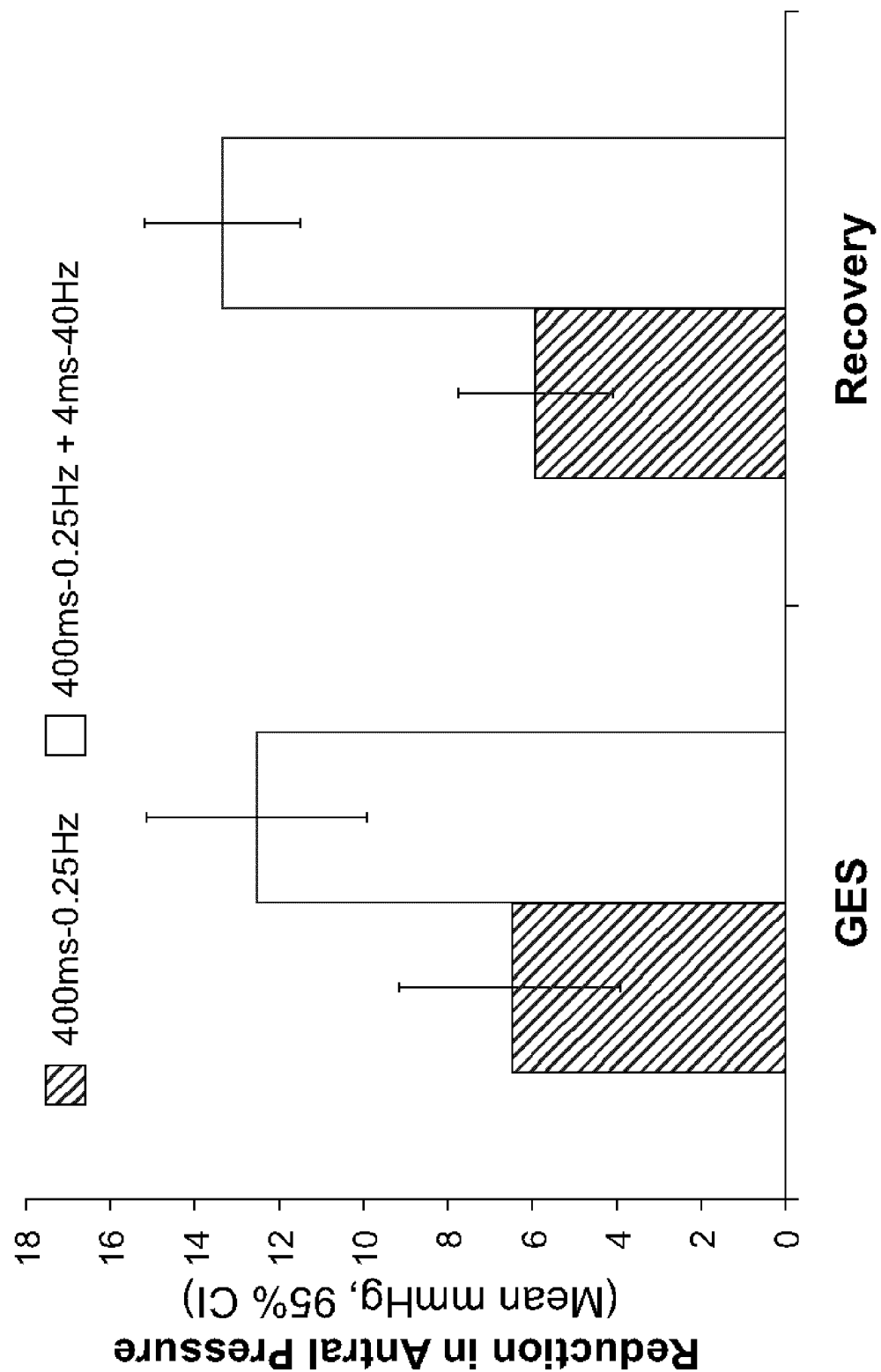
FIG. 11 is a bar graph comparing the reduction in antral pressure using a long pulse GES setting and the combination GES setting during both application of GES and during recovery in lean canines.

FIG. 11 graphically compares the reduction in antral pressure using a long pulse GES setting and the combination GES setting during both application of GES and during recovery in lean canines. As seen in FIG. 11, relative to stimulation pulses having a pulse width of 400 milliseconds and a pulse rate of 0.25 Hz alone, the combination setting produced a greater reduction in mean postprandial antral pressure relative to pre-GES levels (12.5 mmHg vs. 6.5 mmHg). During the recovery period, mean postprandial antral pressure remained significantly higher for the combination setting.

Figure 12:
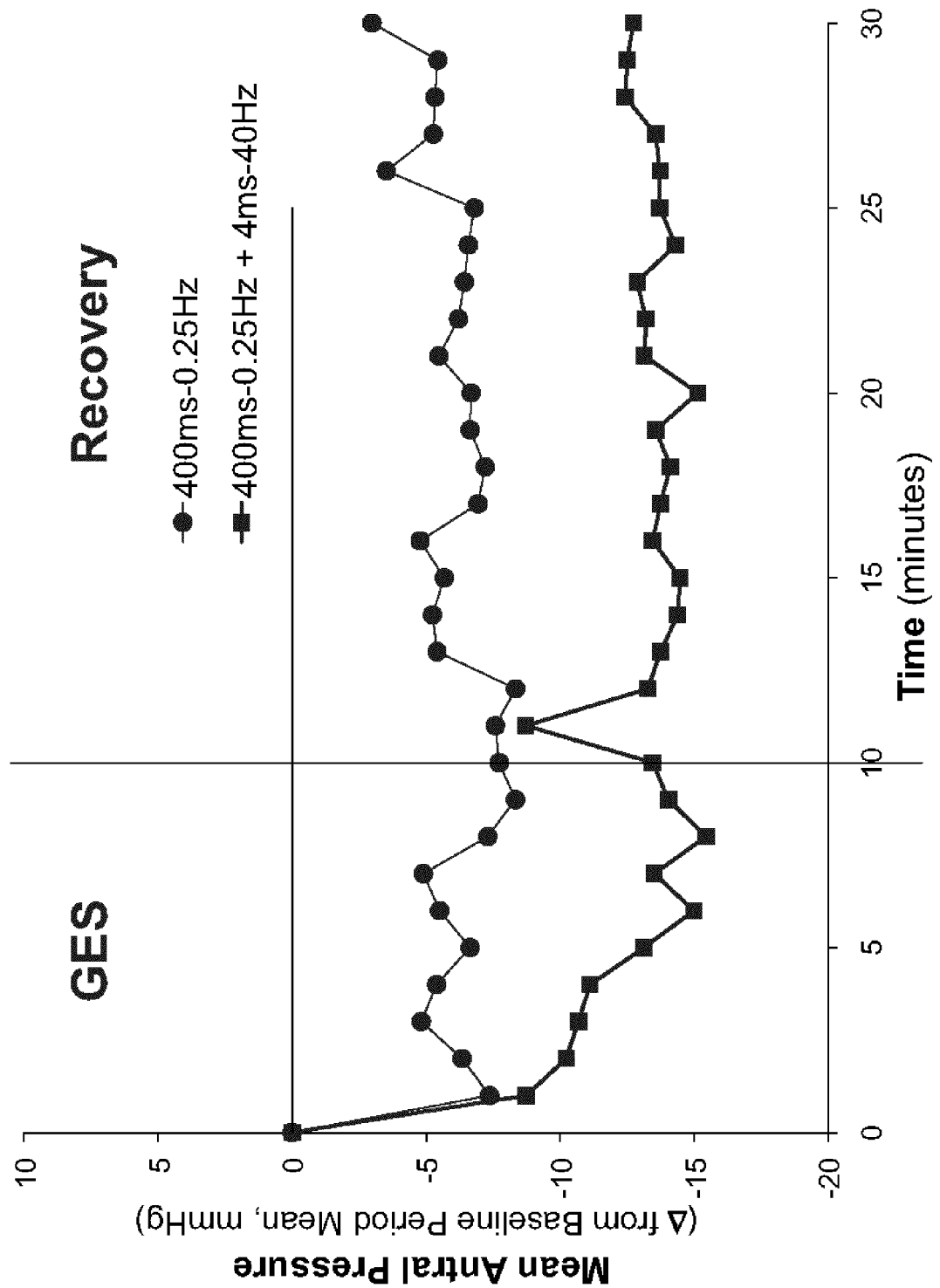
FIG. 12 is a graph depicting the mean antral pressure as a percentage of change from the baseline period mean over a period of 30 minutes, including the GES period and the recovery period using a long pulse setting and a combination pulse setting in lean canines.

FIG. 12 graphically depicts the mean antral pressure as a percentage of change from the baseline period mean over a period of 30 minutes, including the GES period and the recovery period in lean canines. As seen in FIG. 12, the combination setting produced a greater percentage change in mean antral pressure from the baseline period mean than the long pulse GES setting.

Figure 13:
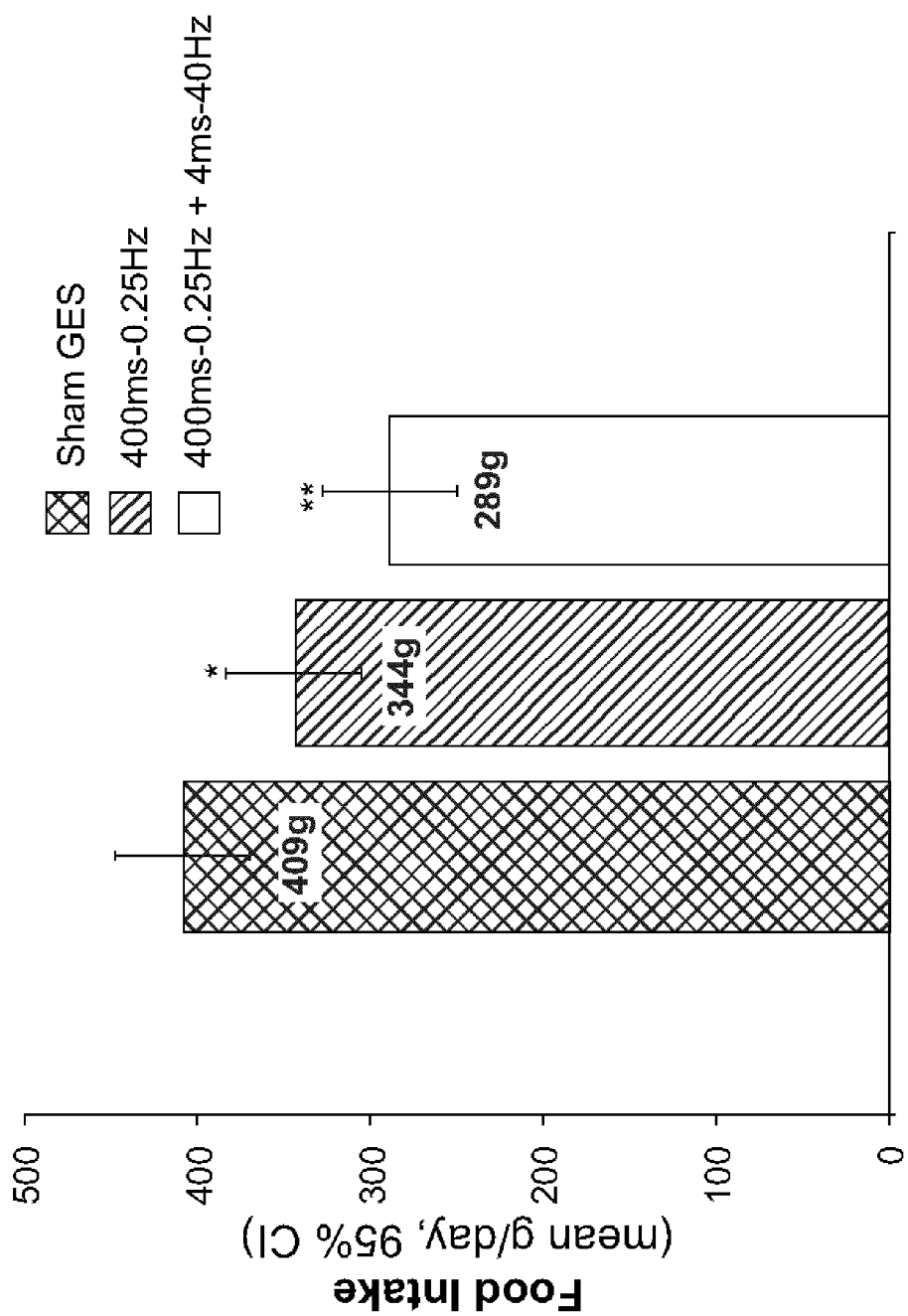
FIG. 13 is a bar graph depicting the food intake in mean grams per day for sham GES, a long pulse setting, and a combination pulse setting in obese rats.

FIG. 13 depicts the food intake in mean grams per day for sham GES, the long pulse setting, and the combination pulse setting in obese rats. The phrase "sham GES" indicates that alligator clip wires were attached to external leads as though GES was to be delivered, but GES was never activated. Again, in the study, a long pulse setting refers to a pulse having a pulse width of 400 milliseconds and a pulse rate of 0.25 Hz. A short pulse burst setting refers to a pulse burst with each pulse of the pulse burst having a pulse width of 4 milliseconds, a pulse rate of 40 Hz, and a duty cycle of 2 seconds ON and 2 seconds OFF. And, a combination setting refers to the combination of a long pulse setting and a short pulse burst setting, having a long pulse with pulse width of 400 milliseconds and a pulse rate of 0.25 Hz and a short pulse burst with each pulse of the pulse burst having a pulse width of 4 milliseconds, a pulse rate of 40 Hz, and a duty cycle of 2 seconds ON and 2 seconds OFF, with long pulses centered between short pulse bursts. Relative to stimulation pulses having a pulse width of 400 milliseconds and a pulse rate of 0.25 Hz alone (long pulses), the combination setting produced greater reduction in food intake (289 grams vs. 344 grams, or 29% vs. 16%) relative to sham-GES control treatment (409 grams).

Figure 14:
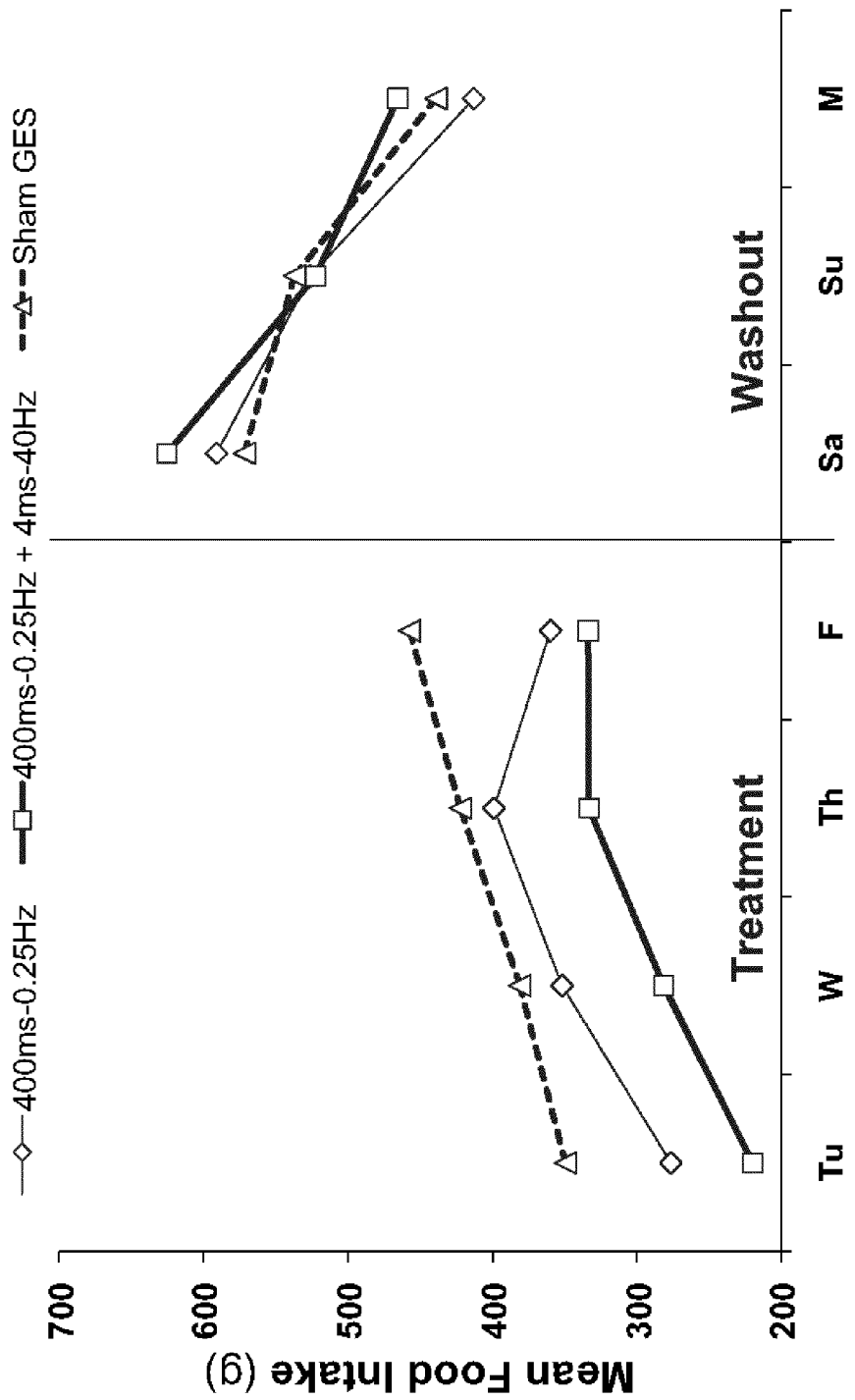
FIG. 14 is a graph comparing the mean food intake in grams using sham GES, a long pulse setting, and a combination setting over seven days in lean canines.

FIG. 14 graphically compares the mean food intake in grams using sham GES, the long pulse setting, and the combination setting over seven days in lean canines Treatment using the stimulation pulses described above occurred from Tuesday through Friday, followed by a washout period from Saturday through Monday. As seen in FIG. 14, the combination setting resulted in a smaller food intake than either the long pulse setting or the sham GES, with the results of the combination setting remaining stable over the treatment period. Interestingly, during the washout period, the results of sham GES, the long pulse setting, and the combination setting converge on Monday to the sham GES results that were seen on Friday. The convergence may indicate a "wire effect" resulting from the attachment of the wire leads to the subjects on Monday.

When combined, long pulse GES and short pulse GES may act additively to enhance acute GI and food intake responses to GES. Combining GES modalities that alter feeding via differing pathways such as vagal nerve afferent pathways and smooth muscle fiber stimulation may be one method for improving the efficacy of GES as an obesity treatment.

Of course, the specific example described above with respect to the canine study is only one example of an electrical stimulation waveform having a repeating pattern of a long pulse followed by a short pulse burst followed by a long pulse followed by a short pulse burst, etc. that may be used to treat obesity. The stimulation waveform is not limited to the specific stimulation parameters described above. Rather, implantable stimulator 12 is configured to deliver stimulation pulses using stimulation parameters within certain operating ranges.

In some examples, stimulator 12 delivers short pulses (forming a short pulse burst) with each pulse having a pulse width in a range of approximately 2 milliseconds to approximately 20 milliseconds. In other examples, the pulse width is in a range of approximately 2 milliseconds to approximately 10 milliseconds. In further examples, the pulse width is in a range of approximately 2 milliseconds to approximately 5 milliseconds.

In one example, stimulator 12 delivers short pulses at a pulse rate in range of approximately 2 Hz to approximately 90 Hz. In other examples, the pulse rate is in a range of approximately 2 Hz to approximately 40 Hz. In further examples, the pulse rate is in a range of approximately 5 Hz to approximately 25 Hz.

In some examples, stimulator 12 delivers long pulses with each long pulse having a pulse width in the range of approximately 100 milliseconds to approximately 600 milliseconds. In other examples, the pulse width is in a range of approximately 200 milliseconds to approximately 550 milliseconds. In further examples, the pulse width in the range of approximately 300 milliseconds to approximately 500 milliseconds.

In one example, stimulator 12 delivers long pulses at a pulse rate in range of approximately 0.1 Hz to approximately 1 Hz. In other examples, the pulse rate is in a range of approximately 0.15 Hz to approximately 0.8 Hz. In further examples, the pulse rate is in a range of approximately 0.2 Hz to approximately 0.4 Hz.

In some examples, stimulator 12 delivers stimulation pulses with a pulse current amplitude in a range between approximately less than 1 milliamp and approximately 20 milliamps. In other examples, the pulse current amplitude is in a range between approximately 1 milliamp and approximately 15 milliamps. In further examples, the pulse current amplitude is in a range between approximately 5 milliamps and approximately 9 milliamps.

In other examples, stimulator 12 delivers stimulation pulses with a pulse voltage amplitude in a range between approximately 3 volts and approximately 12 volts. In other examples, the pulse voltage amplitude is in a range between approximately 4 volts and approximately 10 volts. In further examples, the pulse voltage amplitude is in a range between approximately 5 volts and approximately 8 volts.

In one example, stimulator 12 delivers short pulse bursts for a duration between approximately 0.5 seconds and approximately 20 seconds. In one example, the pulse burst is delivered between a range of approximately 5 seconds and approximately 15 seconds. In some examples, the short pulse burst is delivered between a range of approximately 10 seconds and approximately 12 seconds. The duration of the short pulse burst may be dependent upon the pulse rate of the long pulses. That is, it may be desirable for stimulator 12 to complete delivery of the short pulse burst before delivering the next long pulse. In some examples, however, the delivery of the short pulse burst and long pulses may overlap. For example, separate electrode pairs may be used to deliver short pulse bursts and long pulses, thereby allowing a long pulse to be delivered while short pulse bursts are still being delivered, or short pulse bursts to be delivered while a long pulse is still being delivered.

In some examples, stimulator 12 delivers short pulse bursts immediately following long pulses, with approximately zero delay between long and short pulse bursts. Or, in other examples, there may be a delay between a trailing edge of the long pulse and a rising edge of the short pulse burst. The delay between the trailing edge of the long pulse and the rising edge of the short pulse burst is a function of the duty cycle of the short pulses. The delay may be extended as long as necessary, so long as the short pulse burst finishes before the next long pulse begins. However, in some examples, the delivery of the short pulse bursts and long pulses may overlap, as mentioned above. In some examples, the short pulse bursts may be centered between the long pulses. In other examples, however, the short pulse bursts may immediately follow the long pulse with approximately zero delay. In further examples, the long pulse may immediately follow the short pulse burst with approximately zero delay.

In some examples, the interval between the trailing edge of the long pulse and the rising edge of the short pulse burst may be in a range between approximately 0 seconds and approximately 10 seconds. In other examples, the interval between the trailing edge of the long pulse and the rising edge of the short pulse burst may be in a range between approximately 500 milliseconds and approximately 1 second.

In some examples, the interval between the trailing edge of the short pulse burst and the rising edge of the long pulse may be in a range between approximately 0 seconds and approximately 10 seconds. In other examples, the interval between the trailing edge of the short pulse burst and the rising edge of the long pulse may be in a range between approximately 500 milliseconds and approximately 1 second.

In one example, a short pulse burst with each pulse of the short pulse burst having a pulse width of 4 milliseconds may be used in combination with a long pulse having a 400 millisecond pulse width.

In another study, an obese rat model was used to test whether combining a long pulse, low frequency GES paradigm with a short pulse, high frequency GES paradigm produces a large reduction in food intake than either alone. Using 20 obese male Sprague-Dawley rats (aged 16-17 weeks, mean weight: 568 grams, range: 485-684 grams), the effect of long pulse, low frequency stimulation was compared to the effect of short pulse, high frequency pulse trains alone, and the combination of long pulse, low frequency and short pulse, high frequency pulse trains. The combination of long pulse, low frequency and short pulse, high frequency pulse trains is similar to the electrical stimulation waveform shown and described above with respect to FIGS. 8A and 8B.

During the study, platinum-iridium electrodes were implanted in the gastric antrum of the rat subjects. Lead wires were externalized on the subjects' backs for connection to an external pulse generator. The subjects were acclimated to feed for 2 hours per day in a restrainer to allow GES delivery during feeding. The subjects received 5 days of each treatment in randomized order, separated by 2 day washouts. The treatments included the following: sham GES; a long pulse setting having a pulse width of 400 milliseconds, a pulse rate of 0.25 Hz, and a pulse amplitude of 6 mA; a short pulse burst setting with each pulse of the pulse burst having a pulse width of 4 milliseconds, a pulse rate of 40 Hz, a duty cycle of 2 seconds ON and 2 seconds OFF, and a pulse amplitude of 6 mA; and, a combination setting that combines a long pulse setting and a short pulse burst setting, having a long pulse with pulse width of 400 milliseconds, a pulse rate of 0.25 Hz, and a pulse amplitude of 6 mA and a short pulse burst with each pulse of the pulse burst having a pulse width of 4 milliseconds, a pulse rate of 40 Hz, a duty cycle of 2 seconds ON and 2 seconds OFF, and a pulse amplitude of 6 mA. At necropsy, the rats were randomized (n=9-10 per group) to receive sham GES or GES using the combination setting for 90 minutes before sacrifice and after a 2.5 gram solid meal. Harvested stomachs were used to measure gastric volume and emptying effects of the GES using the combination setting.

Figure 15:
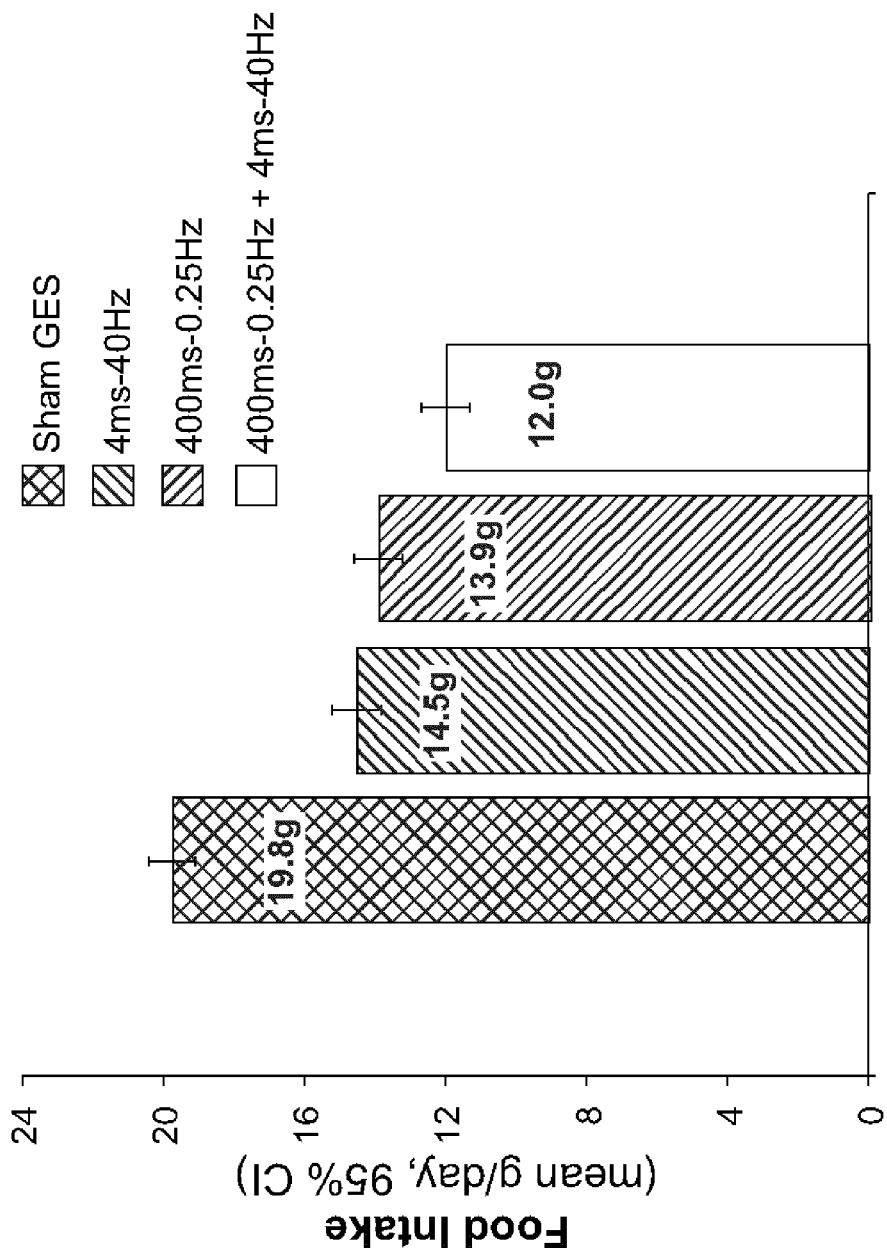
FIG. 15 is a bar graph depicting the food intake in mean grams per day for sham GES, a short pulse setting, a long pulse setting, and a combination setting in obese rats.

FIG. 15 depicts the food intake in mean grams per day for sham GES, the short pulse setting, the long pulse setting, and the combination setting in obese rats. Relative to the sham GES (19.8 grams), mean daily food intake induced by electrical stimulation was reduced 26.7% to 14.5 grams upon application of stimulation pulses with a short pulse burst setting with each pulse of the pulse burst having a pulse width of 4 milliseconds, a pulse rate of 40 Hz, a duty cycle of 2 seconds ON and 2 seconds OFF, and a pulse amplitude of 6 mA. Relative to the sham GES, mean daily food intake induced by electrical stimulation was reduced by 29.8% to 13.9 grams upon application of stimulation pulses with a long pulse setting having a pulse width of 400 milliseconds, a pulse rate of 0.25 Hz, and a pulse amplitude of 6 mA.

Notably, under application of the combination setting stimulation pulses having a long pulse with pulse width of 400 milliseconds, a pulse rate of 0.25 Hz, and a pulse amplitude of 6 mA and a short pulse burst with each pulse of the pulse burst having a pulse width of 4 milliseconds, a pulse rate of 40 Hz, a duty cycle of 2 seconds ON and 2 seconds OFF, and a pulse amplitude of 6 mA, mean daily food intake induced by electrical stimulation was reduced by 39.3% to 12.0 grams relative to the sham GES. Also, although feeding suppression was greater under application of the combination setting stimulation pulses than under application of either the long pulse stimulation setting or short pulse stimulation setting alone, feeding suppression did not differ across the long pulse stimulation setting or short pulse stimulation setting alone treatments.

Figure 16:
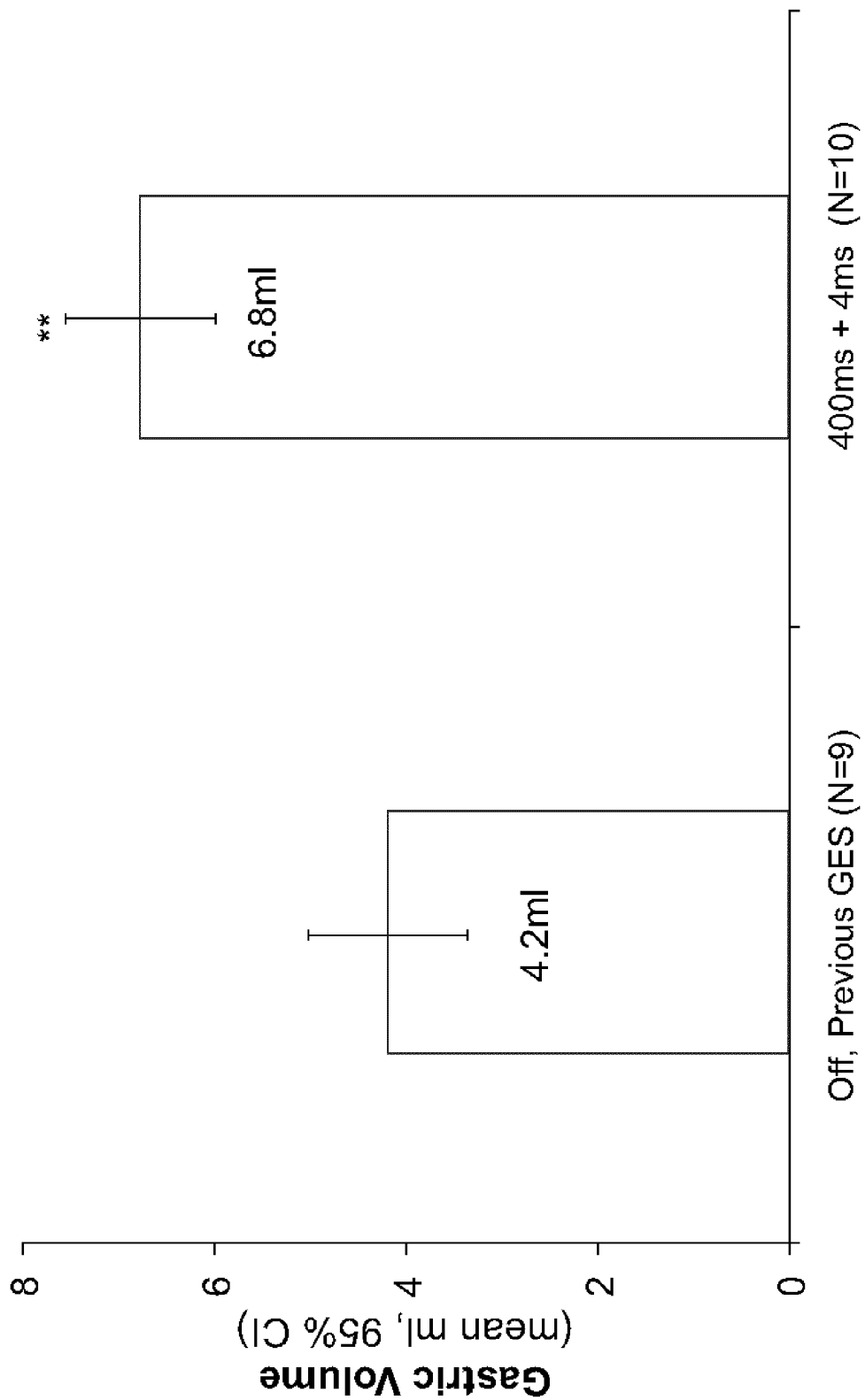
FIG. 16 is a bar graph depicting gastric volume in mean milliliters when GES treatment is off and when using a combination setting treatment in obese rats.

FIG. 16 graphically depicts gastric volume in mean milliliters when GES treatment is off and using a combination setting treatment in obese rats. After 90 minutes of application of the combination GES setting stimulation pulses having a long pulse with pulse width of 400 milliseconds, a pulse rate of 0.25 Hz, and a pulse amplitude of 6 mA and a short pulse burst with each pulse of the pulse burst having a pulse width of 4 milliseconds, a pulse rate of 40 Hz, a duty cycle of 2 seconds ON and 2 seconds OFF, and a pulse amplitude of 6 mA, post-mortem gastric volume was higher (6.8 ml) than after sham GES (4.2 ml).

Figure 17:
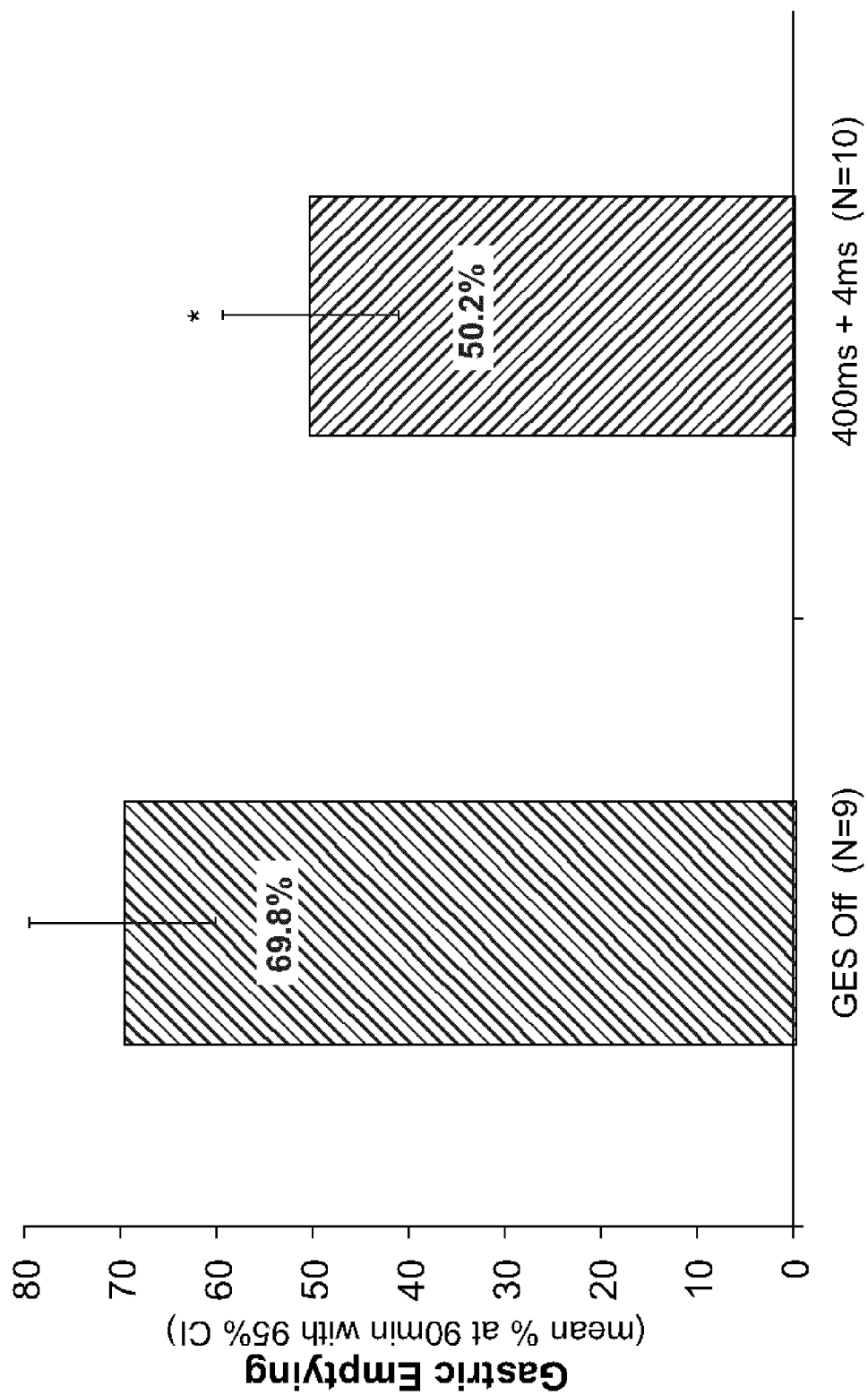
FIG. 17 is a bar graph depicting the mean percentage of gastric emptying at 90 min with 95% Cl when GES is off and when using a combination GES setting stimulation pulses in obese rats.

FIG. 17 graphically depicts the mean percentage of gastric emptying at 90 min with 95% CI when GES is off and when using the combination GES setting stimulation pulses in obese rats. After 90 minutes of application of the combination GES setting stimulation pulses, test meal emptying was lower (50.2%) than after sham GES (69.8%).

Figure 18:
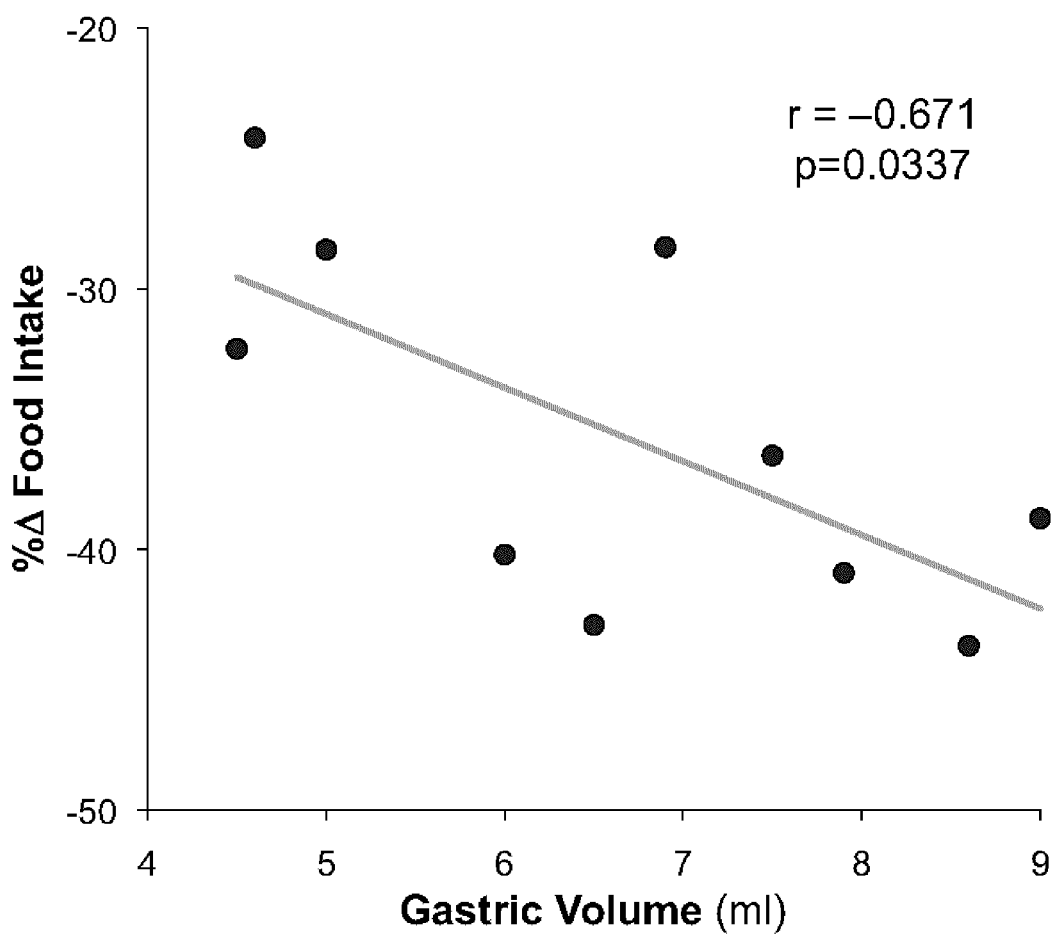
FIG. 18 is a graphic depicting the correlation between GES induced reductions of food intake and gastric volume following GES treatment in obese rats.

FIG. 18 is a graphic depicting the correlation between GES induced reductions of food intake and gastric volume following GES treatment in obese rats. FIG. 18 depicts the percentage food intake (y-axis) compared to the gastric volume (x-axis) in milliliters in obese rats. The graph shows the correlation between changes in food intake from sham-GES control levels under the combination GES setting treatment during the food intake cross-over experiment with post-mortem gastric volume in 10 rats from the cross-over study sample that received 90 minutes of combination GES setting treatment just before sacrifice. These 10 rats had significantly higher mean post-mortem gastric volumes (6.8 ml vs. 4.2 ml) than the 9 remaining cross-over study rats who were assigned to receive only sham-GES during the 90 minutes before necropsy. This difference reflects the gastric distension induced by active GES treatment. The scatter plot of FIG. 18 shows that the degree of GES-induced gastric distension, which is reflected in total gastric volume, correlates with the food intake effect of GES, with food intake suppression tending to be greater in rats with greater gastric volume. The correlation suggests that gastric distension may be a useful acute response marker for the food intake reduction efficacy of GES treatments, and may also be part of the mechanism by which GES reduces food intake. As compared to the preceding cross-over study, higher gastric volume application of the combination GES setting stimulation pulses was associated with a larger food intake reduction using the combination setting treatment, while gastric emptying did not correlate significantly with food intake response. Combining GES modalities that alter feeding via differing pathways may be one means for improving the efficacy of GES as an obesity treatment. Exaggeration of the receptive gastric distension response to food intake may be one mechanism by which GES inhibits feeding.

Of course, the specific example described above with respect to the obese rat study is only one example of an electrical stimulation pulse train having a repeating pattern of a long pulse followed by a short pulse burst followed by a long pulse followed by a short pulse burst, etc. that may be used to treat obesity. The electrical stimulation waveform is not limited to the specific stimulation parameters described above. Rather, implantable stimulator 12 is configured to deliver stimulation pulses using stimulation parameters with certain operating ranges. The ranges of stimulation parameters are substantially similar to those described above with respect to the canine study described immediately above in which the effect of long pulse, low frequency stimulation was compared to the effect of short pulse, high frequency pulse trains alone, and the combination of long pulse, low frequency and short pulse, high frequency pulse trains.

In one example, the long pulse in the electrical stimulation pulse train having a repeating pattern of a long pulse followed by a train of short pulses followed by a long pulse followed by a train of short pulses, etc. may be approximated using a short pulse train, as shown and described above with respect to FIGS. 5A-5B, for example.

The stimulation pulses described above may be unipolar pulses (e.g., delivered from a lead electrode and referenced to an electrode carried or formed by a housing of implantable stimulator 12) or bipolar pulses (e.g., delivered from a lead electrode and referenced to another electrode on the lead). In addition, the stimulation pulses described above may be "alternating monophasic rectangular pulses" or simply "alternating monophasic pulses," as shown and described below with respect to FIG. 19.

Figure 19A:
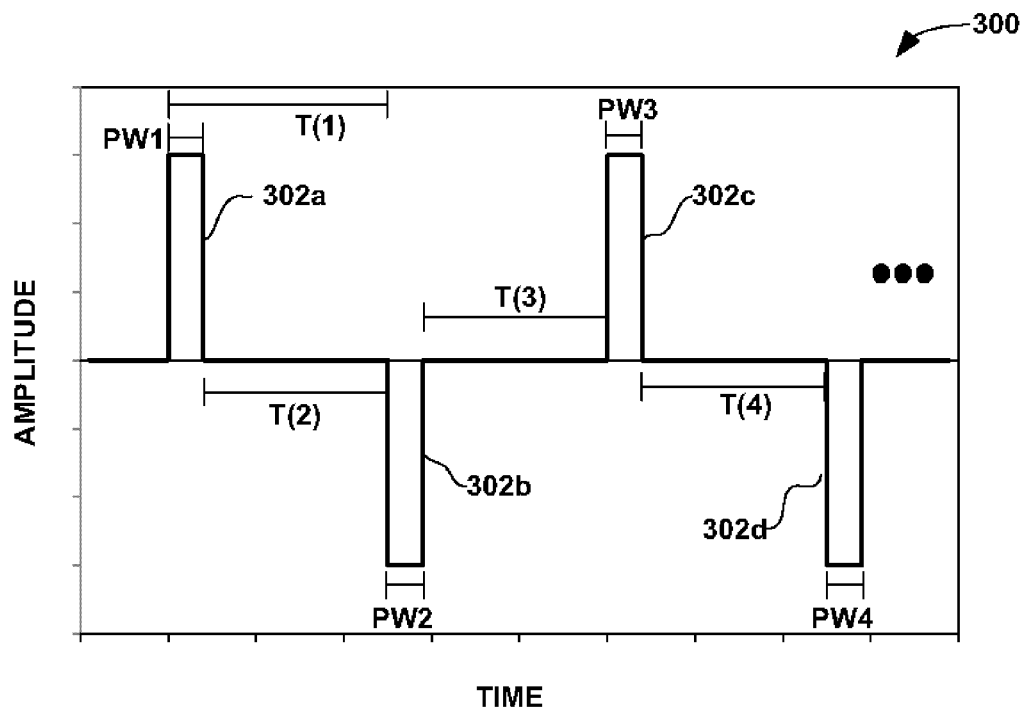
FIGS. 19A and 19B are plots illustrating example waveforms that represent example series of electrical stimulation for delivery to a patient.

FIG. 19A is a plot illustrating an example waveform 300 representing an example series of electrical stimulation pulses for delivery to patient 16. In particular, first stimulation pulse 302a, second stimulation pulse 302b, third stimulation pulse 302c, and fourth stimulation pulse 302d (collectively "series of stimulation pulses" 302) are represented by waveform 300. Waveform 300 may be referred to as an "alternating monophasic rectangular pulses" or "alternating monophasic pulses." Implantable stimulator 12 may generate and deliver gastric electric stimulation to stomach 22 of patient 16 via electrodes 24 and 26 carried on leads 18 and 20 respectively, where the gastric electric stimulation includes the series of electrical stimulation pulses 302 represented by waveform 300. In some examples, such electric stimulation may effectively treat one or more patient conditions, e.g., by increasing the distension of stomach 22 of patient 16. Although series of stimulation pulses 302 represented by waveform 300 are shown to include four stimulation pulses 302a-d, the gastric electric stimulation generated and delivered to patient 16 by implantable stimulator 12 may include any number of stimulation pulses that provide effective treatment to patient 16.

As represented by waveform 300, implantable stimulator 12 delivers first stimulation pulse 302a, second stimulation pulse 302b, third stimulation pulse 302c, and fourth stimulation pulse 302d in direct succession with one another and in the order listed. In the series of stimulation pulses 302, each pulse has a polarity that is opposite of the polarity of the directly preceding pulse and the directly following pulse. For example, as delivered by implantable stimulator 12, first stimulation pulse 302a has a first polarity, which may be either anodic or cathodic, second stimulation pulse 302b has a polarity opposite from that of first pulse 302a, third stimulation pulse 302c has a polarity opposite from that of second stimulation pulse 302b, and so forth.

As seen in waveform 300 of FIG. 19, a time interval that is greater than zero separates each respective pulse in the series of pulses 302. For example, a time interval T(2) greater than zero separates the trailing edge of first pulse 302a and leading edge of second pulse 302b. Similarly, a time interval T(3) greater than zero separates the trailing edge of second pulse 302b and leading edge of third pulse 302c.

It should also be noted that pulses 302a-302d of waveform 300 do not form coupled pulse pairs with one another. A coupled pair of electrical stimulation pulses may include a first electrical stimulation pulse of one polarity (anodic or cathodic) followed immediately, or with some fixed delay, by second electrical stimulation pulse of opposite polarity. When the coupled pair of electrical stimulation pulses are charge balanced, the charge of the first pulse is equal to but opposite of that of the charge of the second pulse. Notably, unlike uncoupled pulses, the timing of the delivery of two stimulus pulses that are coupled to one another is fixed. Instead of forming coupled pulse pairs, the temporal relationship between each individual pulse in the series of pulses in FIG. 19A is dependent on the stimulation pulse frequency. In particular, time intervals T(2), T(3) and T(4) depend on the frequency that the series of pulses are delivered and the pulse width (PW) of each pulse. If series of pulses 302 are delivered at an increased frequency while the pulse width is constant, then time intervals T(2), T(3) and T(4) all decrease. Conversely, if series of pulses 302 are delivered at a decreased frequency while the pulse width is constant, then time intervals T(2), T(3) and T(4) all increase.

In some examples, time intervals T(2), T(3) and T(4) may be substantially equal to one another such that pulses 302a-d are evenly spaced. In other examples, time interval T(2) may be different than that of time interval T(3) and/or time interval T(4). However, in each case, time intervals T(2), T(3) and T(4) are dependent on the frequency at which the series of pulses 302 are delivered since none of pulses 302a-302d form coupled pulse pairs (none of time intervals T(2), T(3) and T(4) are fixed). In examples in which T(2), T(3) and T(4) are approximately equal to one another and pulses 302a-302d each have approximately the same pulse width, the pulse frequency of series of pulses 302 may be determined by the time interval between the leading edge of each pulse, e.g., time interval T(1) between first pulse 302a and second pulse 302b. In some examples, the interpulse interval between directly successive pulses is not less than the pulse width of the successive pulses. For example, time interval T(2) may be greater than or equal to PW1 and PW2. In some examples, the interpulse intervals defined by the series of pulses 302 (i.e., time intervals T(2)-T(4)) may be greater than approximately 1 millisecond, such as, e.g., greater than 2 milliseconds or greater than 10 milliseconds or greater than 50 milliseconds. The interpulse interval between each of pulses 302a-302d is dependent on the pulse frequency and pulse width that the series of pulses 302a-302d are delivered.

The overall charge of the series of pulses 302 of waveform 300 may be approximately zero. The charge of each pulse is dependent on the amplitude and pulse width of each respective pulse of the series of pulses 302. In some examples, the pulse width and amplitude of each respective pulse 302a-d may be selected such that the charge of first pulse 302a may be approximately equal to and opposite of that of the charge of second pulse 302b, and the charge of third pulse 302c may be approximately equal to and opposite of that of the charge of fourth pulse 302d. In some examples, each pulse of the series of pulses 302 may have approximately the same amplitude and pulse width. In other examples, the pulse width and amplitude may differ between pulses. In any case, the series of pulses 302 may be described as charged balanced even though the first pulse 302a is not followed substantially immediately by a second pulse 302b with an equal and opposite charge. Instead, second pulse 302b is delivered after time interval T(2) greater than zero after the end first pulse 302a.

As mentioned above, waveform 300 may be referred to as representing "alternating monophasic rectangular pulses" or simply "alternating monophasic pulses". The interval between every successive pulse of opposite polarity in waveform 300 of FIG. 19 may vary with the pulse frequency selected. This is because each pair of adjacent rectangular pulses with opposite polarity in waveform 300 are two uncoupled stimulus pulses, rather than some of the pulses forming coupled pulse pairs. An increase in pulse frequency for the alternating monophasic waveform 300 will cause the intervals between successive stimulus pulses of opposing polarity to decrease in duration, while a decrease in the selected pulse frequency will cause these intervals between successive pulses of opposite polarity to increase.

In accordance with the techniques of this disclosure, short pulse bursts may be used to approximate or simulate first pulse 302a, third pulse 302c, and so forth, in the manner described above with respect to FIGS. 5A and 5B. Stimulation parameters that may be used to generate a short pulse burst were described in detail above and will not be described again. In some examples, a short pulse burst may also be used to approximate or simulate second pulse 302b, fourth pulse 302d, and so forth, in the manner described above with respect to FIGS. 5A and 5B. Or, in other examples, rather than using a short pulse burst to approximate or simulate second pulse 302b, fourth pulse 302d, and so forth, each of second pulse 302b, fourth pulse 302d, and so forth may be a long pulse.

Figure 19B:
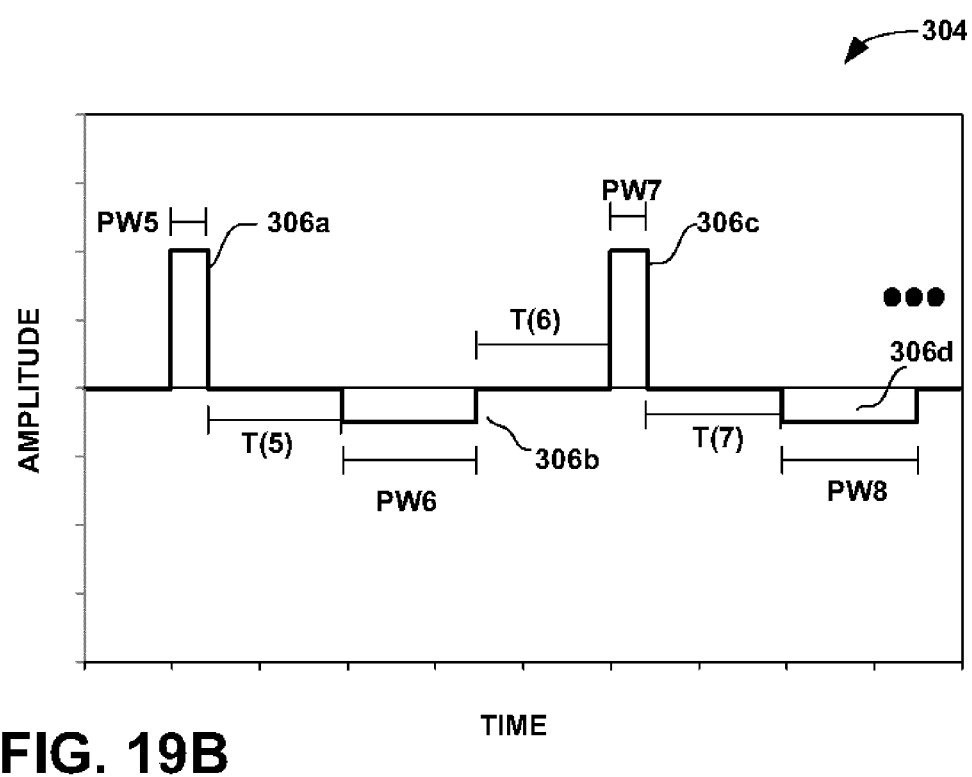

FIG. 19B is a plot illustrating an example waveform 304 representing an example series of electrical stimulation pulses for delivery to patient 16. In particular, first stimulation pulse 306a, second stimulation pulse 306b, third stimulation pulse 306c, and fourth stimulation pulse 306d (collectively "series of stimulation pulses" 306) are represented by waveform 304. The series of pulses 306 of waveform 304 are substantially the same as the series of pulses 302 of waveform 300 in FIG. 19A. For example, none of pulses 306a-306d form coupled pulses with each other. Instead, the temporal relationship between each of 306a-306d is dependent on the frequency at which the series of pulses 66 is delivered. In some examples, time intervals T(5), T(6) and T(7) may be substantially the same, and may vary based on the frequency at which the series of pulses 306 are delivered to patient 16. However, unlike that shown in FIG. 19A, the pulse width and pulse amplitude of the series of pulses 306 is not the same for each respective pulse 306a-d. In particular, first pulse 306a and third pulse 306c have substantially the same amplitude, which is greater than the amplitude of second pulse 306b and fourth pulse 306d, which also have substantially the same amplitude. Moreover, the pulse width PW5 of first pulse 306a and pulse width PW7 of third pulse 306c are substantially the same and less than that of the pulse width PW6 of second pulse 306b and pulse width PW8 of fourth pulse 306d, which are also substantially the same as one another. Despite the difference in pulse widths and pulse amplitudes, the pulse width and amplitude of each respective pulse may be selected such that the series of pulses 306 are substantially charge balanced. For example, first pulse 306a may have substantially the same but opposite charge from the charge of second pulse 306b.

Implantable stimulator 12 may deliver the series of pulses represented by waveforms 300 and 304 to patient 16, e.g., to stomach 22, according to any suitable value for each of pulse width, pulse amplitude, and pulse frequency. In some examples, one or more of the stimulation parameters may be selected such that the electrical stimulation delivered by implantable stimulator 12 to stomach 22 of patient 16 causes the distension of stomach 22 to increase.

In some examples, such pulses may be delivered via a lead-borne electrode (e.g., as a cathode) and an implantable stimulator housing electrode (can electrode) (e.g., as an anode) in a unipolar arrangement, or between bipolar or multipolar lead-borne electrodes. Furthermore, such pulses may be delivered as a continuous pulse train, or the pulses may be contained in periodic or aperiodic bursts of multiple pulses, or in periodic or aperiodic pulse burst envelopes containing multiple pulse bursts. The pulse bursts may be of the same duration or different durations. In some examples, implantable stimulator 12 may deliver electrical stimulation with a burst frequency between approximately 2 and approximately 15 bursts per minute. In some examples, implantable stimulator 12 may deliver bursts having a duration of between approximately 0.1 seconds and approximately 15 seconds.

In accordance with the techniques of this disclosure, a short pulse burst may be used to approximate or simulate first pulse 306a, third pulse 306c, and so forth, in the manner described above with respect to FIGS. 5A and 5B. Stimulation parameters that may be used to generate a short pulse burst were described in detail above and will not be described again. In some examples, a short pulse burst may also be used to approximate or simulate second pulse 306b, fourth pulse 306d, and so forth, in the manner described above with respect to FIGS. 5A and 5B. Or, in other examples, rather than using a short pulse burst to approximate or simulate second pulse 306b, fourth pulse 306d, and so forth, each of second pulse 306b, fourth pulse 306d may be a long pulse.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented partially in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure. Even when implemented in software, the functionality described in this disclosure is implemented in a hardware device, such as a processor that executes the instructions.

Various examples of the invention have been described. These and other examples are within the scope of the following claims.

The invention claimed is:

1. A method comprising:
generating electrical stimulation including a first electrical stimulation pulse and a plurality of pulse bursts, wherein the first electrical stimulation pulse has a duration greater than approximately 100 milliseconds, each of the pulse bursts having a duration of greater than approximately 100 milliseconds, wherein each of the pulse bursts includes a plurality of second pulses, each of the second pulses having a pulse width of approximately 2 milliseconds to approximately 20 milliseconds; and
applying the electrical stimulation to a gastrointestinal tract of a patient to cause gastric distention, wherein applying the electrical stimulation includes application of the electrical stimulation pulse followed by at least one of the plurality of pulse bursts.

2. The method of claim 1, wherein at least one of the following applies:
the plurality of second pulses are delivered at a frequency of approximately 2 hertz to approximately 90 hertz; and
each of the plurality of second pulses has a pulse current amplitude of approximately 1 milliamp to approximately 15 milliamps.

3. The method of claim 1, wherein applying the plurality of pulse bursts to a gastrointestinal tract of a patient comprises applying the plurality of pulse bursts to a stomach of the patient.

4. The method of claim 3, wherein applying the plurality of pulse bursts to a stomach of the patient comprises applying the plurality of pulse bursts to at least one of a lesser or greater curvature of the stomach of the patient.

5. The method of claim 1, wherein at least one of the following applies:
the plurality of second pulses of each pulse burst is are delivered at a frequency of approximately 5 hertz to approximately 50 hertz;
the first electrical stimulation pulse and the one of the plurality of pulse bursts each have a pulse current amplitude of approximately 1 milliamp to approximately 15 milliamps; and
the electrical stimulation is applied by repeating the application of the electrical stimulation pulse followed by at least one of the plurality of pulse bursts.

6. An implantable gastric stimulator comprising:
an electrical stimulation pulse generator configured to generate electrical stimulation including a first electrical stimulation pulse and a plurality of pulse bursts, wherein the first electrical stimulation pulse has a duration greater than approximately 100 milliseconds, each of the pulse bursts having a duration of greater than approximately 100 milliseconds, wherein each of the pulse bursts includes a plurality of second pulses, each of the second pulses having a pulse width of approximately 2 milliseconds to approximately 20 milliseconds; and
one or more electrodes, coupled to the pulse generator, configured to apply the electrical stimulation to a gastrointestinal tract of the patient to cause gastric distention, and wherein electrical stimulation pulse generator is configured to apply the first electrical stimulation pulse followed by at least one of the plurality of pulse bursts.

7. The stimulator of claim 6, wherein at least one of the following applies:
the plurality of second pulses are delivered at a frequency of approximately 2 hertz to approximately 90 hertz; and
each of the plurality of second pulses has a pulse current amplitude of approximately 1 milliamp to approximately 15 milliamps.

8. The stimulator of claim 6, wherein the one or more electrodes configured to apply the plurality of pulse bursts to a gastrointestinal tract of a patient are configured to apply the plurality of pulse bursts to a stomach of the patient.

9. The stimulator of claim 8, wherein the one or more electrodes configured to apply the plurality of pulse bursts to a stomach of the patient are further configured to apply the second stimulation pulses to at least one of a lesser or greater curvature of the stomach of the patient.

10. The stimulator of claim 6, wherein at least one of the following applies:
the plurality of second pulses of each pulse burst are delivered at a frequency of approximately 5 hertz to approximately 50 hertz;
the first electrical stimulation pulse and respective second pulses of the plurality of pulse bursts each have a pulse current amplitude of approximately 1 milliamp to approximately 15 milliamps; and
the electrical stimulation pulse generator applies the electrical stimulation by repeating the application of the first electrical stimulation pulse followed by one of the plurality of pulse bursts.

* * * * *